US007135562B2

(12) United States Patent
Horseman et al.

(10) Patent No.: US 7,135,562 B2
(45) Date of Patent: Nov. 14, 2006

(54) AVIAN IFABP GENE EXPRESSION CONTROLLING REGION

(75) Inventors: Nelson D. Horseman, Cold Spring, KY (US); Scott L. Pratt, Athens, GA (US)

(73) Assignee: University of Cincinnati, Cincinnati, OH (US)

( * ) Notice: Subject to any disclaimer, the term of this patent is extended or adjusted under 35 U.S.C. 154(b) by 255 days.

(21) Appl. No.: 10/099,663

(22) Filed: Mar. 14, 2002

(65) Prior Publication Data

US 2003/0177516 A1    Sep. 18, 2003

(51) Int. Cl.
*C07H 21/04* (2006.01)
*C12N 15/63* (2006.01)
*C12N 15/85* (2006.01)
*C12N 15/00* (2006.01)

(52) U.S. Cl. .................. 536/24.1; 435/320.1; 435/325; 435/70.1

(58) Field of Classification Search ................ 536/24.1; 435/325, 320.1, 70.1
See application file for complete search history.

(56) References Cited

U.S. PATENT DOCUMENTS

| | | | |
|---|---|---|---|
| 4,237,224 | A | 12/1980 | Cohen et al. |
| 4,603,112 | A | 7/1986 | Paoletti et al. |
| 4,722,848 | A | 2/1988 | Paoletti et al. |
| 4,769,330 | A | 9/1988 | Paoletti et al. |
| 4,833,080 | A | 5/1989 | Brent et al. |
| 5,162,215 | A | 11/1992 | Bosselman et al. |
| 5,174,993 | A | 12/1992 | Paoletti |
| 5,175,384 | A | 12/1992 | Krimpenfort et al. |
| 5,338,683 | A | 8/1994 | Paoletti |
| 5,494,807 | A | 2/1996 | Paoletti et al. |
| 5,505,941 | A | 4/1996 | Paoletti |
| 5,580,859 | A | 12/1996 | Felgner et al. |
| 5,589,466 | A | 12/1996 | Felgner et al. |
| 5,591,639 | A | 1/1997 | Bebbington |
| 6,156,569 | A | 12/2000 | Ponce de León et al. |

FOREIGN PATENT DOCUMENTS

| | | |
|---|---|---|
| WO | WO 87/05325 | 3/1986 |
| WO | WO 92/06180 | 10/1990 |
| WO | WO 92/19749 | 5/1991 |
| WO | WO 92/20316 | 5/1991 |
| WO | WO 92/22635 | 6/1991 |
| WO | WO 93/04701 | 9/1991 |
| WO | WO 93/25234 | 6/1992 |
| WO | WO 94/06920 | 9/1992 |
| WO | WO 94/11524 | 11/1992 |
| WO | WO 97/47739 | 6/1996 |
| WO | WO 99/19472 | 10/1997 |
| WO | WO 99/42569 | 2/1998 |

OTHER PUBLICATIONS

Sugano Malaria cDNA library *Plasmodium falciparum* 3D7 cDNA, Accession No. AU088319, Jan. 27, 2001.*
Homo sapiens clone RP11-24F22, Accession No. AC026485, Mar. 22, 2000.*
Cloning of a cDNA Encoding Rat Intestinal Fatty Acid Bidning Protein, Alpers et al; Proc. Natl. Acad. Sci USA 81:313-317(1984).
Consecutive Events of Growth, Differentiation and Death of the Small Intestinal Epithelial Cell Line, IEC-6, Ametani et al.;, In vitro Cell Dev. Biol. Anim. 32:127-130 (1996).
Intestinal Fatty Acid Binding Protein Gene Expression Reveals the Cephalocaudal Patterning During Zebrafish Gut Morphogenesis, Andre et al; Int. J Dev. Biol; 44:249-252 (2000).
Gut specific expression using mammalian promoters in transgenic *Xenopus laevis*, Beck et al; Mech. Dev. 88:221-227 (1999).
Cellular and molecular aspects of fat metabolism in the small intestine, Besnard et al; Proc. Nutr. Soc. 55:19-37 (1996).
Suppression subtractive hybridization: A method for generating differentially regulated or tissue-specific cDNA probes and libraries, Diatchenko et al; Proc. Natl. Acad. Sci. USA 93:6025-6030 (1996).
Suppression Subtractive Hybridization: A Versatile Method for Identifying Differentially Expressed Genes, Diatchenko et al; Methods in Enzymology 303:349-380 (1999).
Regulation of cholesterol esterification by micellar cholesterol in CaCo-2 cells, Field et al; J. Lipid Res. 28:1057-1066 (1987).
Distinct Functions Are Implicated for the GATA-4,-5,and -6 Transcription Factors in the Regulation of Intestine Epithelial Cell Differentiation, Gao et al; Mol. Cell Biol. 18:2901-2911 (1998).
The Nucleotide Sequence of Rat Liver Fatty Acid Binding Protein mRNA, Gordon et al; J. Biol. Chem. 258:3356-3363 (1983).
The Mouse Intestinal Fatty Acid Binding Protein Gene: Nucleotide Sequence, Pattern of Developmental and Regional Expression, and Proposed Structure of Its Protein Product, Green et al; DNA Cell Biol. 11:31-41 (1992).
Structure and Localization of the Gene Encoding Human Peripheral Myelin Protein 2 (PMP2), Hayasaka et al; Genomics 18:244-248 (1993).
A Review of Intestinal Fatty Acid Binding Protein Gene Variation and the Plasma Lipoprotein Response to Dietary Components, Hegele, R.A.; Clin Biohcem. 31:609-612 (1998).

(Continued)

*Primary Examiner*—Celine Qian
(74) *Attorney, Agent, or Firm*—Kyle D. Yesland

(57) ABSTRACT

A recombinant nucleic acid is provided having an avian promoter. One embodiment of the present invention contemplates the use of a gut-specific promoter, wherein a promoter can be the chicken intestinal fatty acid binding protein promoter region. A method for making a transgenic bird is also disclosed by transfecting a bird with a vector comprising a recombinant nucleic acid comprising a chicken intestinal fatty acid binding protein promoter region operably linked to a heterologous nucleic acid expressing a desired polypeptide to be expressed in the gut tissue of an avian.

31 Claims, 4 Drawing Sheets

OTHER PUBLICATIONS

Activation of a member of the steroid hormone receptor superfamily by peroxisome proliferators, Issemann et al; Nature 347:645-650 (1990).

Fibronectin Synthesis by Epithelial Crypt Cells of Rat Small Intestine, Quaroni et al; Proc. Natl. Acad. Sci. USA 75:5548-5552 (1978).

Comparison of the Patterns of Expression of Rat Intestinal Fatty Acid Binding Protein/Human Growth Hormone Fusion Genes in Cultured Intestinal Eipthelial Cell Lines and in the Gut Epithelium of Transgenic Mice, Rottman et al; J. Biol. Chem 268:11994-12002 (1993).

Expression of rat intestinal fatty acid binding protein in *E. coli* and its subsequent structural analysis: a model system for studying the molecular details of fatty acid-protein interaction, Sacchettini et al; Mol. Cell. Biochem. 98:81-93 (1990).

Cell Migration Pathway in the Intestinal Epithelium: An In Situ Marker System Using Mouse Aggregation Chimeras, Schmidt et al; Cell 40:425-429 (1985).

Fatty acid binding protein isoforms: structure and function, Schroeder et al; Chem Phys. Lipids; 92:1-25 (1998).

Thyroid Hormone-Dependent Regulation of the Intestinal Fatty Acid-Binding Protein Gene during *Amphibian metamorphosis*, Shi et al; Dev. Biol 161:48-58 (1994).

Isolation and expression of a cDNA for huma brain fatty acid-binding protein (B-FABP), Shimizu et al; Biochim Biophys Acta. 1354:24-28 (1997).

A 20-nucleotide element in the intestinal fatty acid binding protein gene modulates its cell lineage-specific, differentiation-dependent, and cephalocaudal patterns of expression in transgenic mice, Simon et al; Proc. Natl. Acad. Sci. USA 92:8685-8689 (1995).

The Human and Rodent Intestinal Fatty Acid Binding Protein Genes. A Comparative Analysis of Their Structure, Expression, and Linkage Relationships, Sweetser et al; J. Biol. Chem. 262:16060-16071 (1987).

Transgenic Mice Containing Intestinal Fatty Acid-Binding Protein-Human Growth Hormone Fusion Genes Exhibit Correct Regional and Cell-Specific Expression of the Reporter Gene in Their Small Intestine, Sweetser et al; Proc. Natl. Acad. Sci. USA 85:9611-9615 (1988).

Mechanisms underlying generation of gradients in gene expression within the intestine: an analysis using transgenic mice containing fatty acid binding protein-human growth hormone fusion genes, Sweetser et al; Genes Dev. 2:1318-1332 (1988).

\* cited by examiner

```
Human       MAFDSTWKVDRSENYDKFMEKMGVNIVKRKLAAHDNLKLTIT
Mouse       ....G......N...E........I.VM....G.........
Chick       ...NG...IEKN...E....A....VM....G.........Q
Xenopus     ....G..........E....V..........G......VI.Q
Zebra fish: .T.NG......N...E....Q....M............I.LE
```

Fig. 1

```
AGCTTCCTCTGCGCAGAAAGGCTGTGGGGTTCTTGTTCCCTCACACAGCTTAAGCAAATCCCCAAGTTCAAAAACGTCGGCTGTGTAAGAGGAGATGGCTCAC        100
TTCAAATGAAGTGAATTATGAAATAATCATAAAACGAGCTCTGTTGGCAGATCAGAGATAACCTCTGCTGTGGACATAACCTCTTAAAGTGTATAGGTAGAA        200
CAGGAGGTGTTTGCAACTAGATGTACCACATTGATCTTCTAGGAGACAAAAGGGTCTGAAACAAATAATTCTGGTGCACAGTCAGT                      300
AGCAGCCTGTTTTGGGTGCAACTACAGCAACTTGTTTGCAACAATAACAATCTAAGTTGTTTCTCTTTTCCTCTTAACTTCTGTACAGTCTAAAG            400
GTGAAGAGTAGCTATTGAGTTACTTCCCTCTGCATCCTCTTAGCCAGATTAGCATTGATTTCAAAATGAACCTGAGTGGAATGGAAAGCCACACTATTTT        500
GGTATCACCAGCAAAGTTCTAAATTTATAGTTATACTTCAGTAAAACCTTTGCTGCAGGTCTGGAAGAAAAGAAGATTATGATAACACCAGACTAGTA         600
AAATTCATTAGTTAGAGCCAACCTGTATCTGTGATAAGCAACATTCAGCATTCCAGATTTACATTTTGAAGCTAATAGACAGCAGATTTG                  700
GTGCCGTCCATAGGAACAGACTAACTATATAACCTGAGTTTAGTACAAGCAGATTTAGCACCAGAACATTTGCTCAGTTTCAGTAGCACTATCTTGTGCG       800
GAAGAAGGAGCTGAGCCAGTGTGTGCTCATTTCTGCATTATCCTTCAACATTTAAAACCTGGGATCTATGGAAATCAAACACGTTGGGTAAAATTCACT         900
TAGCAGCACATCAACTACTGTAGGAATGGACACAGAAACAGCATTCACTGAGAAATGGCTATAATATAGAGAAGGTGTCCTGAATTTAGACTA             1000
CCTATTAAAGAGTGAGGACACGAATGGAGAATATCATCGCAATTTCGTAGCTAGACTCAGCACTCGCAAGCTTCTGAAACTGAACCGAGTTTCCCAAAC        1100
TACCTGTGGATGTTCAGTGGATCCTTCATCTCATGCTTATTATGTGGAGTAGAATAGATTCTCACCAAATTAGAATGGACAAAGCAGAGATTTGTGTTTT      1200
ATCTGTGGGTAAATACGTTTCTCCAGTTGTATAAAGACCCTCCCACCAGTATAAAGTCCTATGCAACAAAGAAAATGTCAATACATTCTCTTAGTCTC         1300
ATTATTATTTTCATTAGATAGCCCGGTTTTTTTACTACAACTCAAATAAGATGAACAGAGTAATGGGTTAGTGACTGTTTATAAAGAAGAGTAATAAAGAT      1400
ACTATCATCATTTGAGGCAATAAGGGAGGAGAGATTCAGCAGAAGATTGCTTACCAAGTTAAACTAAAGTGACCCCCCTCCTTGACAA                    1500
GATCAATGCCACAGTTGAGCTTTAGCCAGCCACATCATCATGTAAATTGCTTCCTGATAAGCCTGTTCTTCATAAATTCTCTTTGCAAAGCTCTGCTACTTA   1600
CCAGAAGTCTGCCTACAGACAGAAGATGGCATTTAACGGTACTTGGAAATAGAAAAATTCATGAAGCAATATGAGAAAATTCATGAAGCAATGGGTAAGCC    1700
TTACTTTTTTGAATGCCTTCTAAAGCAGATATCCACTTATTTGAAAGACTCCTATTTGCCCTGCACATTGCCCTTGCACATTCGATTTTATTTGCATTGCG     1800
CTGCTATTTTGCCCTTGCACATTGCCCTTGCACATTCGATTTTATTTGCATTGCG                                                   1900
ATAATCTTATGCATTAGCTAATTGCTGGTCTCCAGTTTGCAGAGGCATTCCAGCAGAACACATGGAGCAGAACATGGGAATAACAGACTCTATAGAGGG        2000
ATTACAAGAGGGAATTGCTGGTCTCCAGTTTGCAGAACACATGGAGCAGAACACATGGGAATAACAG                                       2100
CTGTAATATGGATGTAAACATAACATACCTAGTTGGATAGTAGTTGTATTACAGGCTGAACACTGCCTCAGTGAAAGGTGGAGAAGAGTAAGACTCTGA        2200
GTCAGAATTCGGGCTAAGCTCCCTCAACTACAGAAAAAGTCACAATAAAAATGCAAACATGATGTTCATTTTGTTTTTCTCTGCTTGATGTTAATTGA        2300
TTTATTATTATTTTTTTTTTTAGGCGTGAATGTGATGAAAAGAAAAGTTAGGAGCCCACGATAATCTGAAGCTCACTATTCAG                         2381
```

Fig. 2

SEQ ID NO: 2

ATTATTATTTTCATTAGATAGCCGGTTTTTTACTACAACTCAAATAAGATGAACAGAATG
AATGGGTTAGTGACTGTTTATAAAGAAGAGTAATAAAGATACTATCATCATTTGAGGCAA
TAAGGGAGGGAGAGATTCAGCAAACAGTGTGCTTACAAGTGGAAAACAAGTTAAACTAAA
GTGACCCCCCTCCTTGACAAGATCAATGCCACAGTTGAGCTTTAGCCAGCCACATCATCA
TGTAAATTGCTTTCCTGATAAGCCTGTTCATAAATTCTCTTTGCAAAGCTCTGCTACTTA
CCAGAAGTCTGCCTACAGACAGAAAGATGGCATTTA

FIG. 3

AVIAN IFABP GENE EXPRESSION CONTROLLING REGION

FIELD OF THE INVENTION

The present invention relates generally to a novel avian promoter that regulates tissue-specific protein expression. More specifically, the invention relates to a promoter that, in avians, regulates gut-specific expression of a nucleotide sequence under the control of the promoter as, for example, a nucleotide sequence that imparts disease resistance.

BACKGROUND

Genetic engineering techniques that provide for transferring a foreign, or exogenous, gene into a host's genome resulting in the production of a transgenic animal are among the most powerful tools available for the study of genetics and the understanding of genetic mechanisms. Although the field of transgenics was initially developed to understand the action of a single gene in the context of the whole animal and the phenomena of gene activation, expression, and interaction, this technology has shown great promise from an economic perspective. The use of transgenic technology to convert animals into "protein factories" for the production of specific proteins or other substances of pharmaceutical interest (Gordon et al., 1987, *Biotechnology* 5: 1183–1187; Wilmut et al., 1990, *Theriogenology* 33: 113–123) offers significant advantages over more conventional methods of protein production by gene expression. Likewise, the incorporation of an exogenous gene to produce an improved production animal could have important implications as, for example, in the production of a disease resistant bird.

Regulation signals, such as promoters and terminators, that allow ordered transcription are required to express foreign genes efficiently. Terminator sequences, located on the 3' end of the encoding DNA, can serve to end transcription and, if appropriate, as a signal for polyadenylation of the mRNA formed. Promoter sequences, responsible for the expression of the foreign gene, contain recognition sequences for RNA-polymerases and for transcriptional effectors.

A large number of promoters suitable for controlling the expression of foreign genes axe known. For example, one of the most frequently used promoters, the cytomegalovirus immediate-early promoter, is described in U.S. Pat. No. 5,168,062 to Stinski. Because the CMV promoter provides for constitutive expression, a gene product under its regulation is expressed in most, if not all tissues.

Inducible or tissue-specific promoters may be employed to provide more selective gene expression. For example, U.S. Pat. No. 6,084,089 to Mine et al., discloses a promoter that induces gene expression at low temperatures in potato tubers, but which is scarcely induced at normal temperatures. Ryals et al., in U.S. Pat. No. 5,689,044, claim a chemically inducible promoter of a plant PR-1 gene, while a vector having a promoter that is inducible by methanol or glycerol is described in U.S. Pat. No. 5,750,372 to Sakai et al.

Examples of cell- and tissue-specific promoters include, inter alia, the following: a muscle-specific promoter associated with a avian retroviral vector described by Petropoulos, et al. (1992); a defective DNA viral vector having a neural tissue-specific promoter useful for in vivo expression of a gene (U.S. Pat. No. 6,040,172 to Kaplitt); an LPT2 promoter having aleurone-tissue specific activity (U.S. Pat. No. 5,525,716 to Olsen et al.); and promoters causing leaf-specific expression in plants, as disclosed by Sonnewald et al. in U.S. Pat. No. 6,229,067.

The failure of traditional methods such as vaccination and chemoprophylaxis in preventing avian infections associated with significant enteric pathogens such as *Salmonella* spp. makes producing disease resistant birds through transgenic technology an attractive option. A gene coding for an antimicrobial peptide and incorporated into a bird's genome could be capable of inhibiting the proliferation of a pathogen via specific or non-specific means. Novel peptides having antimicrobial activity, and DNA sequences encoding such peptides, include inter alia: purified bovine granulocyte peptide A and murine granulocyte peptide A (U.S. Pat. No. 6,008,195 to Selsted); antimicrobial peptides derived from lentiviruses (U.S. Pat. No. 5,945,507 to Montelaro et al.); DNA encoding biocidal proteins isolated from seeds which exhibit antifungal and antibacterial activity (U.S. Pat. No. 5,691,199 to Broekaert et al.); and an antimicrobial composition from a prokaryotic DNA extract (U.S. Pat. No. 6,096,719 to Matsutani et al.).

By placing the gene coding for an antimicrobial peptide under the control of a gut-specific promoter undesired side-effects associated with expressing the antimicrobial protein in a ubiquitous fashion can be minimized. In addition, a promoter capable of gut-specific expression would be useful when operably linked to other genes, especially those encoding proteins optimally localized to the gastrointestinal tract.

One means of identifying promoters exhibiting gut-specificity is by examining protein production in avian intestinal tissue. One such suitable candidate is intestinal fatty acid-binding protein (iFABP). The product of the FABP2 gene, iFABP is a member of a family of intracellular lipid-binding proteins and probably involved in the absorption and intracellular transport of dietary long-chain (C16–C20) fatty acids in the small intestine (Sacchettini et al., 1990; Schroeder et al., 1998; Hegele, 1998).

Members of the homologous, low molecular weight (15 kD), cytosolic lipid-binding proteins likely arose from an ancestor gene by repeated gene duplication, and include lipid-binding proteins specific to the liver, intestinal tissue, heart, ileal and adipocyte tissue, epidermis, brain, retinal tissue, retinoic acid, or peripheral myelin (Gordon et al., 1983; Alpers et al., 1984; Hayasaka et al., 1993; Shimizu et al., 1997; Schroeder et al., 1998). The tissue distributions of these gene products differ and are strictly regulated. Expression of iFABP, for example, is limited to the small intestinal epithelium, especially enterocytes and goblet cells, and not found in Paneth cells in the crypts or enteroendocrine cells (Sweetser et al., 1988a), even though all four types of cells originated from an identical stem cell (Schmidt et al., 1985).

Gene expression largely depends on the combination of the gene promoter sequence and transcription factors, and FABP promoters have provided one of the best models for studying tissue-specific gene regulation and cell differentiation in vertebrates. A cis-acting promoter sequence for iFABP has been characterized in mammals (rat, mouse, and human) and amphibia (Xenopus) (Sweetser et al., 1987; Green et al., 1991; Gao et al. 1998). The sequences located between nucleotides −277 and +28 (or more concisely −103 and +28) from the transcription start site appear to be important for directing gut- and cell type-specific expression of the rat iFABP gene (Sweetser 1988a, b; Rottman and Gordon, 1993). That this region of the rat iFABP promoter can direct tissue-specific gene expression in a transgenic frog suggests conservation of the regulatory mechanism of iFABP expression among vertebrates (Beck and Slack, 1999). Several elements in the proximal 0.3 kb region have been nominated as regulatory sequences involved in tissue specific expression of iFABP, particularly in the rat. For example, a 14-bp element composed of two direct 7-bp repeats is conserved among the gene promoters of several small intestine-specific genes in mammals. Two members of the steroid hormone receptor superfamily, HNF-4 and ARP-1 are reported to bind to the iFABP promoter element (Issemann and Green, 1990; Rottman and Gordon, 1993).

The amphibian iFABP gene promoter lacks a peroxisome proliferator-responsive element (PPRE)-homologous element, and the importance of this element and transcriptional factors in the tissue-specific expression of iFABP, therefore, is obscure. It has been suggested that binding of GATA-4 and -5 to a proximal GATA-binding site is involved in tissue specific expression of the iFABP gene in vitro (Gao et al., 1998). However, gene activation by these transcription factors is modest, and additional cell-specific factors are probably required for in vivo regulation.

A 20-bp cis-acting element that regulates cell lineage-specific patterns of iFABP expression has been identified by promoter mapping studies in transgenic mice (Simon et al., 1995). This element, located from −263 to −244 in the rat FABP2 gene, binds small intestinal nuclear proteins and acts as a suppressor of gene expression in iFABP-negative intestinal epithelial cells such as colon epithelium, and cells located in the crypts of Lieberkuhn, and the Paneth cell lineage. The short (−277 to +28 bp) promoter of rat iiFABP showed rather weak promoter activity when compared to the long (1.2 kb) promoter in the small intestine and failed to direct expression of the gene in the ileum (Sweetser et al., 1988a). Thus, the proximal 0.3 kb promoter region is very important in the regulation of iFABP gene, but the more distal sequence also contributes to precise control of this gene.

SUMMARY OF THE INVENTION

Briefly described, the present invention relates to novel isolated avian nucleic acids comprising the avian gut-specific gene expression control region associated with the intestinal fatty acid binding protein (iFABP).

The isolated nucleic acids of the present invention are useful for the expression of operably linked heterologous nucleic acid inserts in a transfected avian cell such as, for example, an intestinal cell.

One aspect of the present invention provides novel isolated nucleic acids that are isolated from the region located immediately 5 'upstream of the transcription start sites of the chicken iFARBP locus. The novel isolated avian nucleic acid sequences encoding the gut-specific gene expression control region comprises gene regulatory elements interspersed with stretches of nucleic acid that may serve at least to organize the gene regulatory elements in an ordered array relative to a polypeptide-encoding region. In one embodiment of the present invention the isolated nucleic acids are isolated from a chicken.

The isolated avian gut-specific promoter regions of the present invention are useful for directing tissue-specific expression of a polypeptide-encoding nucleic acid. The isolated avian gut-specific promoter may be operably linked with selected nucleic acid inserts, wherein the nucleic acid inserts encodes polypeptides desired to be expressed in a transfected avian cell. The nucleic acid insert may be placed in frame with a signal peptide sequence. Translation initiation may start with the signal peptide and continue through the nucleic acid insert, thereby producing an expressed polypeptide having the desired amino acid sequence.

The recombinant DNAs of the present invention may further comprise a polyadenylation signal sequence that will allow the transcript directed by the novel iFABP gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like.

The sequence of the expressed nucleic acid insert may be optimized for codon usage by a host cell. This may be determined from the codon usage of at least one, and preferably more than one, protein expressed in a chicken cell. For example, the codon usage may be determined from the nucleic acid sequences encoding the proteins ovalbumin, ovomucoid, ovomucin and ovotransferrin of chicken.

Yet another aspect of the present invention are expression vectors suitable for delivery to a recipient cell for expression of the vector therein. The expression vectors of the present invention may comprise an isolated avian gut-specific gene expression control region operably linked to a nucleic acid insert encoding a polypeptide, and optionally a polyadenylation signal sequence. The expression vectors may further comprise a bacterial plasmid sequence, a viral nucleic acid sequence, or fragments or variants thereof that may allow for replication of the vector in a suitable host.

Another aspect of the present invention is a method of expressing a heterologous polypeptide in a eukaryotic cell by transfecting the cell with a recombinant DNA comprising an avian gut-specific gene expression control region operably linked to a nucleic acid insert encoding a polypeptide and, optionally, a polyadenylation signal sequence, and culturing the transfected cell in a medium suitable for expression of the heterologous polypeptide under the control of the avian gut-specific gene expression control region.

Also within the scope of the present invention are recombinant cells, tissues and animals containing non-naturally occurring recombinant nucleic acid molecules according to the present invention and described above. In one embodiment of the present invention, the transformed cell is a chicken gut-specific cell and the nucleic acid insert comprises the chicken gut-specific iFABP gene expression control region, a nucleic acid insert encoding a polypeptide codon optimized for expression in an avian cell, and an SV40 polyadenylation sequence.

Additional objects and aspects of the present invention will become more apparent upon review of the detailed description set forth below when taken in conjunction with the accompanying figures, which are briefly described as follows.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

FIG. 1 illustrates an amino acid sequence comparison of the N-terminal portion of iFABP of various species of vertebrates. The chick sequence is >70% identical to the other corresponding sequences.

FIG. 2 illustrates the nucleic acid sequence (SEQ ID NO: 1) of the chick iFABP (chiFABP) gene containing 1.6 kbp of 5'-flanking region. The proximal 0.3 kb promoter region comprising the nucleic acid sequence SEQ ID NO: 2 is underlined. Solid circles (●) indicate conserved sequences among vertebrate (human, mouse, chick, and frog iFABP sequences). A TATA-like box, the element associated with GATA factor binding sites, and the element involved in cell-type specific expression of the gene within the gut are in bold. Long single-headed arrows indicate the PCR primers (SEQ ID NOS: 3 and 4) used for the subcloning of the promoter into a luciferase reporter vector. The small arrow with Met indicates the translation starting codon. An intron is also shown in italics between two small angled arrows.

FIG. 3 illustrates the 0.3 kb iFABP promoter sequence SEQ ID NO: 2 indicated by the underlined region in FIG. 1.

DETAILED DESCRIPTION OF THE INVENTION

Figure 4:
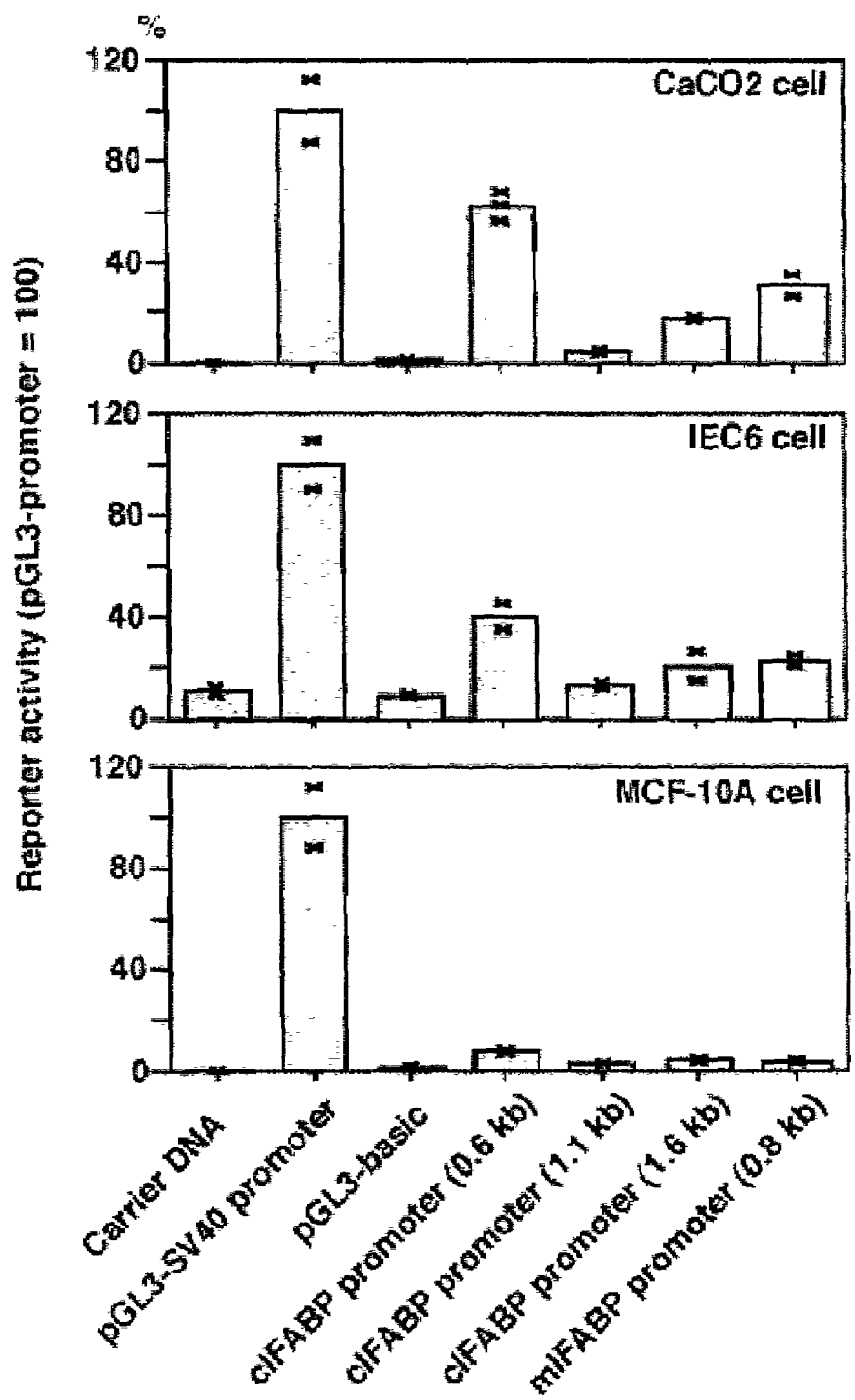
FIG. 4 indicates chick iFABP (chiFABP) and mouse iFABP (miFABP) promoter activity in intestinal (CaCo2 and IEC6) and non-intestinal (MCF10A) cell lines as estimated by the double-luciferase method. The mean value of the activity of the SV40 promoter (pGL3-promoter) was 100%. Columns indicate the mean value of 2–3 samples (shown with "x"). The proximal 0.5 kbp of the chiFABP promoter showed high, modest, and minimal promoter activity in CaCo2, IEC6, and MCF10A cells, respectively. Longer promoters showed modest to minimal promoter activities.

The publications cited herein to clarify the background of the invention and in particular, materials cited to provide additional details regarding the practice of the invention are cited in the following text and are incorporated herein by reference in their entireties.

The present invention is directed toward recombinant nucleic acids comprising a tissue specific promoter, transgenic animals modified by the incorporation of such a recombinant nucleic acid, and methods of tissue specific protein expression in animals. The present invention provides a tissue specific promoter directing protein expression in the gut that, in one aspect of the present invention, is a chicken iFABP promoter.

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications, combination, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

For convenience, certain terms employed in the specification, examples, and appended claims are collected here.

Definitions

The term "animal" is used herein to include all vertebrate animals, including humans. It also includes an individual animal in all stages of development, including embryonic and fetal stages.

The term "avian" as used herein refers to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities. Common turkey breeds include Broad Breasted White and Broad Breasted Bronze, while common duck breeds include Pekin, Rouen, Muscovey, Khaki Campbell and Indian Runner, and common geese breeds include Chinese, Embden, African, and Toulouse. Common qual breeds include Japanese and Button.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes a desired protein.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased. The other DNA may, for example, be derived from a yeast or bacterial genome, or a cloning vector, such as a plasmid or a viral vector. The term significant as used herein is used to indicate that the level of increase is useful to the person making such an increase.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin are suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology, isolated from an appropriate source such as a bird, or are synthesized. The term "polypeptides" further contemplates polypeptides as defined above that include chemically modified amino acids or amino acids covalently or noncovalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "modulates" as used herein refers to the ability of a nucleotide sequence to alter the function of an expressed protein, as for example, by increasing the expression or biological activity potential of the protein.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein or polypeptide or a portion thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently. The term "locus" may also refer to a site created by the insertion of an isolated nucleic acid, such that the protein of interest may be expressed at optimal levels. For example, increased expression levels may result from the insertion of multiple gene copies at a locus. Alternately, the insertion of a locus at a particularly advantageous location in the host genome may result in optimal expression of the protein of interest.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "transcription regulatory sequences" as used herein refers to nucleotide sequences that are associated with a gene nucleic acid sequence and which regulate the transcriptional expression of the gene. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron"

regions, or may be in regions of nucleic acid sequence that are in the region of nucleic acid.

The term "coding region" as used herein refers to a continuous linear arrangement of nucleotides that may be translated into a protein. A full length coding region is translated into a full length protein; that is, as complete a protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, or any other label that is well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a gene of interest or a fragment thereof. Hybridization of the first and second nucleic acids may be conducted under stringent conditions, e.g., high temperature and/or low salt content tending to disfavor hybridization of dissimilar nucleotide sequences. Alternatively, hybridization of the first and second nucleic acid may be conducted under reduced stringency conditions, e.g., low temperature and/or high salt content tending to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in aqueous solution, followed by washing with 1×SSC at 65° Celsius. Formulae to calculate appropriate hybridization and wash conditions to achieve hybridization permitting 30% or less mismatch between two nucleic acid molecules are disclosed, for example, in Meinkoth et al. (1984) *Anal. Biochem.* 138: 267–284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al., eds. "Molecular Cloning: A Laboratory Manual," (2nd ed., 1989, Cold Spring Harbor Press); the contents of which are herein incorporated by reference in their entirety.

Typically, stringent conditions will be those in which the salt concentration is less than about 1.5 M Na ion, typically about 0.01 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary moderate stringency conditions include hybridization in 40 to 45% formamide, 1 M NaCl, 1% SDS at 37° Celsius, and a wash in 0.5× to 1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

The terms "unique nucleic acid region" and "unique protein (polypeptide) region" as used herein refer to sequences present in a nucleic acid or protein (polypeptide) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The terms "percent sequence identity" or "percent sequence similarity" as used herein refer to the degree of sequence identity between two nucleic acid sequences or two amino acid sequences as determined using the algorithm of Karlin and Attschul (1990, *Proc. Natl. Acad. Sci.* 87: 2264–2268), modified as in Karlin and Attschul (1993, *Proc. Natl. Acad. Sci.* 90: 5873–5877). Such an algorithm is incorporated into the NBLAST and XBLAST programs of Attschul et al. (1990, *T. Mol. Biol. Q*15: 403–410). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al. (1997, *Nuc. Acids Res.* 25: 3389–3402). When utilizing BLAST and Gapped BLAST programs, the default parameters of the respective programs (e.g., XBLAST and NBLAST) are used. See http://www.ncbi.nlm.nih.gov.

Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "sense strand" as used herein refers to a single stranded nucleic acid molecule, as for example, a DNA molecule from a genomic DNA that may be transcribed into RNA and translated into the natural polypeptide product of the gene. The term "antisense strand" is used herein to mean the single strand nucleic acid molecule that is complementary with the sense strand.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; or, the antisense transcripts may inhibit transport of the "target RNA", or, the antisense transcripts may inhibit translation of "target RNA".

As used herein "vector" refers to any agent capable of genomic integration and includes plasmids, cosmids, viruses, autonomously replicating sequences, and the like. Suitable viral vectors include but are not limited to retroviruses and replication-defective virus vectors derived from viruses. Viruses suitable for use in the production of transgenic birds include, but are not limited to, avian leukosis virus (ALV); Moloney murine leukemia virus (MLV) pseudotyped with vesicular stomatitis virus G protein (VSV-G); reticuloendotheliosis virus (REV); rous sarcoma virus (RSV); replication-defective vectors derived from these viruses; and the like. For example, a suitable "replication-defective virus" includes viral vectors permitting insertion of a foreign gene into a cell by virtue of an initial infection, but wherein the vectors do not permit reinfection of the cells. One suitable replication-defective virus is the replication-defective REV vector ME11, which is believed to lack all viral structural genes.

The term "nucleic acid vector" as used herein refers to a natural or synthetic single or double stranded plasmid or viral nucleic acid molecule that can be transfected or transformed into cells and replicate independently of, or within, the host cell genome. For example, a circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that may further include at least one regulatory sequence operably linked to a nucleotide sequence coding for the desired protein. Regulatory sequences are well recognized in the art and may be selected to ensure good expression of the linked nucleotide sequence without undue experimentation by those skilled in the art. As used herein, the term "regulatory sequences" includes promoters, enhancers, and other elements that may control expression. Standard molecular biology textbooks such as Sambrook et al., eds. "Molecular Cloning: A Laboratory Manual," (2nd ed., 1989, Cold Spring Harbor Press) may be consulted to design suitable expression vectors, promoters, and other expression control elements. It should be recognized, however, that the choice of a suitable expression vector depends upon multiple factors including, but not limited to, the choice of the host cell to be transformed and the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques as, for example, treating the cells with high concentrations of a salt such as, but not limited to, a calcium or magnesium salt; subjecting the cells to an electric field; detergent treatment; using liposome encapsultation, microinjection, or employing viral-mediated insertion methods; or employing a combination of the above.

The term "transfecting agent" as used herein refers to a composition of matter added to the genetic material for enhancing the uptake of heterologous DNA segment(s) into a eukaryotic cell, preferably an avian cell, and more preferably a chicken male germ cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes can be targeted to the male germ cells using specific ligands that are recognized by receptors on the cell surface of the germ cell, such as the c-kit ligand or modifications thereof.

Other preferred transfecting agents include, but are not limited to, lipofectin, lipofectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, and poly(ethylenimine) (PEI). These non-viral agents have the advantage that they can facilitate stable integration of xenogeneic DNA sequences into the vertebrate genome, without size restrictions commonly associated with virus-derived transfecting agents.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell can harbor a vector that is extragenomic. An extragenomic nucleic acid vector does not insert into the cell's genome. A recombinant cell can further harbor a vector or a portion thereof that is intragenomic. The term intragenomic defines a nucleic acid construct incorporated within the recombinant cell's genome.

The term "recombinant nucleic acid" as used herein refers to combinations of at least two nucleic acid sequences that are not naturally found in a eukaryotic or prokaryotic cell. The nucleic acid sequences may include, but are not limited to nucleic acid vectors, gene expression regulatory elements, origins of replication, sequences that when expressed confer antibiotic resistance, and protein-encoding sequences. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "promoter" refers to a DNA sequence, usually located upstream to a coding sequence, that controls expression of the coding sequence by controlling production of messenger RNA (mRNA) by, for example, providing a recognition site for RNA polymerase and/or other factors necessary for the start of transcription. The term "promoter" further may refer to sequences that contain variations in the native promoter's nucleotide sequence yet retain recognizable characteristics of the native promoter. For example, a promoter may be capable of directing higher protein expression than the native promoter. Promoter derivatives may include nucleotide sequences that are less than the complete sequence of a naturally occurring promoter, but which still control expression of a coding sequence.

As used herein the term "avian promoter" refers to a promoter that naturally occurs in a bird's genome, and including derivatives thereof.

As used herein, the term "gut-specific promoter" refers to a promoter that promotes gene expression in any portion of the gut, and includes derivatives of naturally occurring gut-specific promoters. As used herein "gut" refers to any and all portions of the alimentary canal, and includes organs such as, for example, the crop sac, esophagus, stomach, large intestines, small intestines, gizzard.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, polypeptides that stimulate immune responses include polypeptides that stimulate the proliferation and differentiation of stem cells of the immune system and polypeptides that elicit chemotactic migration of immune cells, such as macrophages and polymorphonuclear cells (neutrophils). Other examples of polypeptides that stimulate immune responses include interleukins and factors such as natural killer cell enhancing factor (NKEF), granulocyte colony stimulating factor (G-CSF), macrophage colony stimulating factor (M-CSF), and granulocyte-macrophage colony stimulating factor (GM-CSF).

The term "hormone," as used herein, refers to a substance normally formed by one organ that stimulates the function of another organ. Polypeptide hormones include, but are not limited to, insulin, growth hormone, gastric inhibitory polypeptide, and cholecystokinin.

Preferred antimicrobial polypeptides are those that are effective against a pathogen including, but not limited to, poultry pathogens. For example, the antimicrobial polypeptide can be effective against a pathogen selected from the group consisting of, but not limited to, salmonella, coccida, or mixed populations thereof.

As used herein, a "transgenic animal" is any animal, such as an avian species, including the chicken, in which one or more of the cells of the avian may contain heterologous nucleic acid introduced by way of human intervention, such as by transgenic techniques well known in the art. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject polypeptide, e.g. either agonistic or antagonistic forms. The terms "chimeric animal" or "mosaic animal" are used herein to refer to animals in which the recombinant gene is found, or in which the recombinant is expressed in some, but not all, cells of the animal. The term "tissue-specific chimeric animal" indicates that the recombinant gene is present and/or expressed in some tissues, but not others.

As used herein, the term "transgene" means a nucleic acid sequence (encoding, for example, a human interferon polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene according to the present invention will include one or more transcriptional regulatory sequences, polyadenylation signal sequences, and any other nucleic acid, such as introns, that may be necessary for optimal expression of a selected nucleic acid.

The techniques used to isolate and characterize the nucleic acids and proteins of the present invention are well known to those of skill in the art and standard molecular biology and biochemical manuals may be consulted to select suitable isolation and characterization protocols without undue experimentation. See, for example, Sambrook et al. eds. "Molecular Cloning: A Laboratory Manual," (2nd ed., 1989, Cold Spring Harbor Press); the contents of which are herein incorporated by reference in its entirety.

Following longstanding law convention, the terms "a" and "an" as used herein, including the claims, mean "one or more."

Abbreviations

Abbreviations used in the present specification include the following: aa, amino acid(s); bp, base pair(s); cDNA, DNA complementary to RNA; nt, nucleotide(s); SSC, sodium chloride-sodium citrate; DMSO, dimethyl sulfoxide.

The present invention provides avian gut-specific promoters useful, for example, in regulating the expression of heterologous nucleic acids in transgenic avians. One aspect of the present invention, therefore, is an isolated nucleic acid having the nucleic acid SEQ ID NO: 1, as shown in FIG. 2, derived from the chicken genome and comprising, in part, the chicken intestinal fatty acid binding protein (chiFABP) promoter having the nucleic acid sequence SEQ ID NO: 2, as shown in FIG. 3. In one embodiment of the present invention, therefore, the promoter is a sequence (SEQ ID NO: 2) isolated from the chicken intestinal fatty acid binding protein promoter and which is smaller than the entire promoter sequence depicted in SEQ ID NO: 1, but which is capable of directing gene expression.

In another embodiment of the present invention, the avian iFABP promoter comprises a first element having the nucleotide sequence TAAAT, a second nucleotide sequence having the nucleotide sequence GATA, a third element having the nucleotide sequence CCACATCA, and a fourth element having the sequence CATCA.

According to one embodiment of the present invention, the chiFABP promoter may comprise a TAAAT sequence located 56 bp upstream of the putative ATG translation initiation codon and which, while not wishing to be bound by any one theory, is believed to form a TATA-like box; a GATA sequence upstream of the TATA-like box; a CCACATCA sequence located about 40 bp upstream of TATA-box; and a CATCA sequence located 167 bp upstream of the TATA-like box.

The chiFABP promoter of the present invention comprises the nucleotide sequence AAGATACTATCATCATT (SEQ ID NO: 5) that may be involved in cell-type specific expression within the gut, and which is a part of the larger nucleotide sequence SEQ ID NO: 2, as shown in FIG. 2. Nucleic acid sequence SEQ ID NO: 2 represents a proximal 0.3 kb promoter region.

In another embodiment of the present invention, the promoter comprises a GATA factor binding site. GATA factors include transcriptional regulatory proteins that interact specifically with DNA cis elements containing GATA, more preferably (A/T) GATA (G/G), or related sequences. Exemplary GATA factors include, but are not limited to, GATA-4, GATA-5, and GATA-6 that are expressed in endoderm-derived tissues including liver, lungs, pancreas and gut. While not wishing to be bound by any one theory, it is believed GATA factors also activate the intestinal fatty acid binding protein promoter.

In one embodiment of the present invention, the isolated nucleic acid comprising the iFABP promoter may be isolated from an avian selected from the group consisting of a chicken, a turkey, a duck, a goose, a quail, a pheasant, a ratite, an ornamental bird or a feral bird.

In another embodiment of the present invention, the isolated iFARBP is obtained from a chicken. In this embodiment, the isolated nucleic acid has the sequence of SEQ ID NO: 1, as shown in FIG. 1B, or a variant thereof Another aspect of the present invention provides nucleic acids that can hybridize under high, medium, or low stringency conditions to an isolated nucleic acid that encodes a chicken iFABP having all, a derivative of, or a portion of the nucleic acid sequence SEQ ID NO: 1 shown in FIG. 1. The nucleotide sequences determined from the isolation of the chiFABP gene expression control region from a chicken (SEQ ID NO: 1) will allow for the generation of probes designed for use in identifying homologs of gut-specific gene expression control regions in other avian species.

Fragments of a nucleic acid encoding a portion of the subject iFABP gene expression control region are also within the scope of the invention. As used herein, a fragment of the nucleic acid encoding an active portion of an avian iFABP gene expression control region refers to a nucleotide sequence having fewer nucleotides than the nucleotide sequence encoding the entire nucleic acid sequences of the iFABP gene expression control region.

In one embodiment of the present invention, the nucleotide sequences of the isolated DNA molecules of the present invention may be used as probes in nucleic acid hybridization assays for the detection of the iFABP gene expression control region. The nucleotide sequences of the present invention may be used in any nucleic acid hybridization assay system known in the art, including, but not limited to, Southern blots (Southern, 1975, *E. M. J. Mol. Biol.* 98: 508), Northern blots (Thomas et al. 1980, *Proc. Natl. Acad. Sci.* 77: 5201–05), and Colony blots (Grunstein et al., 1975, *Proc. Natl. Acad. Sci.* 72: 3961–65). Alternatively, the isolated DNA molecules of the present invention can be used in a gene amplification detection procedure such as, for example, a polymerase chain reaction (Erlich et al., 1991, *Science* 252:1643–51; hereby incorporated by reference in its entirety) or in restriction fragment length polymorphism (RFLP) diagnostic techniques as, for example, described in pgs. 519–522 and 545–547 of Watson et al., *Recombinant DNA,* 2nd ed. (1992, Scientific American Books), which is hereby incorporated by reference.

Nucleotides constructed in accordance with the present invention can be labeled to provide a signal as a means of detection. For example, radioactive elements such as $^{32}P$, $^{3}H$ and $^{35}S$ or the like provide sufficient half-life to be useful as radioactive labels. Other materials useful for labeling synthetic nucleotides include fluorescent compounds, enzymes, and chemiluminescent moieties. Methods useful in selecting appropriate labels and binding protocols for binding the labels to the synthetic nucleotides are well known to those of skill in the art. Standard immunology manuals such as *Promega: Protocol and Applications Guide* 2nd Edition, 1991 (Promega Corp., Madison, Wis., the content of which is incorporated herein in its entirety) may be consulted to select an appropriate labeling protocol without undue experimentation.

Another embodiment of the present invention encompasses isolated nucleic acid molecules that are at least about 75%, preferably at least about 80%, more preferably at least about 85%, even more preferably at least about 90%, still more preferably at least about 95%, and even more preferably at least about 99% identical to a chicken-derived iFABP gene expression control region-encoding nucleic acid molecule as depicted in SEQ ID NO: 1.

In another embodiment of the present invention, an avian iFABP gene expression control region gene or nucleic acid molecule that can be an allelic variant of SEQ ID NO: 1 is disclosed.

The present invention also contemplates the use of antisense nucleic acid molecules that are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized nucleotides can be produced in variable lengths. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill or, alternatively, such nucleotide primers and probes can be purchased commercially from a variety of sources (e.g., Sigma Genosys, The Woodlands, Tex. or The Great American Gene Co., Ramona, Calif.).

The nucleic acid sequence of a chicken iFABP gene expression control region nucleic acid molecule (SEQ ID NO: 1) of the present invention allows one skilled in the art to, for example, (a) make copies of those nucleic acid molecules by procedures such as, but not limited to, insertion into a cell for replication by the cell; by chemical synthesis; or by procedures such as PCR or LCR, (b) obtain nucleic acid molecules that include at least a portion of such nucleic acid molecules, including fall-length genes, full-length coding regions, regulatory control sequences, truncated coding regions and the like, (c) obtain iFABP gene expression control region nucleic acid homologs in other avian species such as, but not limited to, turkey, duck, goose, quail, pheasant, parrot, finch, and ratites including ostrich, emu, and cassowary and, (d) to obtain isolated nucleic acids capable of hybridizing to an avian iFABP gene expression control region nucleic acid and be used to detect the presence of nucleic acid-related sequences by complementation between the probe and the target nucleic acid.

Such nucleic acid homologs can be obtained in a variety of ways including, but not limited to, by screening appropriate expression libraries with antibodies of the present invention; using traditional cloning techniques to screen appropriate libraries; amplifying appropriate libraries or DNA using oligonucleotide primers of the present invention in a polymerase chain reaction or other amplification method; and screening public and/or private databases containing genetic sequences using nucleic acid molecules of the present invention to identify targets. Examples of preferred libraries to screen, or from which to amplify nucleic acid molecules include, but are not limited to, mammalian BAC libraries, genomic DNA libraries, and cDNA libraries. Similarly, preferred sequence databases useful for screening to identify sequences in other species homologous to a chicken iFABP gene expression control region include, but are not limited to, GenBank and the mammalian Gene Index database of The Institute of Genomics Research (TIGR).

Generally, a recombinant nucleic acid of the present invention may comprise an avian gut-specific promoter of the present invention operably linked to a nucleic acid sequence encoding a desired polypeptide. Desired polypeptides suitable for operably linking to the promoters of the present invention include, but are not limited to, a health-promoting polypeptide that provides an antibacterial activity; a polypeptide that may stimulate an immune response; or one that promotes growth and development of the recipient transgenic animal.

Recombinant Nucleic Acids, and Expression Thereof, Under the Control of an Avian iFABP Gene Promoter Another potentially useful application of the novel isolated avian iFABP gene expression control region of the present invention is its use to increase the amount of a heterologous protein present in a bird (especially the chicken) by gene transfer. In most instances, a heterologous polypeptide-encoding nucleic acid insert transferred into the recipient animal host will be operably linked with the iFABP gene expression control region to allow the cell to initiate and continue production of the genetic product protein. A recombinant DNA molecule of the present invention can be transferred into the extra-chromosomal or genomic DNA of the host.

The recombinant DNA nucleic acid molecules of the present invention can be delivered to cells using conventional recombinant DNA technology. The recombinant DNA molecule may be inserted into a cell to which the recombinant DNA molecule is heterologous (i.e., not normally present). Alternatively, as described more fully below, the recombinant DNA molecule may be introduced into cells which normally contain the recombinant DNA molecule in order, for example, to correct a deficiency in the expression of a polypeptide, or where over-expression of the polypeptide is desired.

For expression in heterologous systems, the heterologous DNA molecule is inserted into an expression system or vector of the present invention in proper sense orientation and correct reading frame. The vector contains the necessary elements for the transcription and translation of the inserted protein-coding sequences, including the novel isolated iFABP gene expression control regions.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced to a cell by means of transformation and replicated in cultures, including eukaryotic cells grown in tissue culture.

One aspect of the present invention, therefore, is an expression vector suitable for delivery to a recipient cell for expression of the vector therein. It is contemplated to be within the scope of the present invention for the expression vector to comprise an isolated avian iFABP gene expression control region operably linked to a nucleic acid insert encoding a polypeptide and, optionally, a polyadenylation signal sequence. The expression vector of the present invention may further comprise a bacterial plasmid sequence, a viral nucleic acid sequence, or fragments or variants thereof that may allow for replication of the vector in a suitable host.

The novel isolated avian iFABP gene expression control region of the present invention (SEQ ID NOS: 1) and a polypeptide-encoding nucleic acid sequence operably linked thereto and, optionally, a polyadenylation signal sequence may be introduced into viruses such as, but not limited to, a vaccinia virus. Methods for making a viral recombinant vector useful for expressing a protein under the control of the iFABP promoter are analogous to the methods disclosed in U.S. Pat. Nos. 4,603,112; 4,769,330; 5,174,993; 5,505,941; 5,338,683; 5,494,807; 4,722,848; Paoletti, E. *Proc. Natl. Acad. Sci.* 93:11349–11353 (1996); Moss, *Proc. Natl. Acad. Sci.* 93:11341–11348 (1996); Roizman, *Proc. Natl. Acad. Sci.* 93: 11307–11302 (1996); Frolov et al., *Proc. Natl. Acad. Sci.* 93: 11371–11377 (1996); Grunhaus et al., *Seminars in Virology* 3: 237–252 (1993) and U.S. Pat. Nos. 5,591,639; 5,589,466; and 5,580,859 relating to DNA expression vectors, inter alia; the contents of which are incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference), pQE, pIH821, pGEX, pET series (see Studier, F. W. et. al. (1990) "Use of T7 RNA Polymerase to Direct Expression of Cloned Genes," *Gene Expression Technology*, vol. 185, which is hereby incorporated by reference in its entirety) and derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al. eds. "Molecular Cloning: A Laboratory Manual," (2nd ed., 1989, Cold Spring Harbor Press), which is hereby incorporated by reference in its entirety.

A variety of host-vector systems may be utilized to express the protein-encoding sequence(s). Primarily, the vector system must be compatible with the host cell used. The use of eukaryotic recipient host cells permits partial or complete post-translational modification such as, but not only, glycosylation and/or the formation of the relevant inter- or intra-chain disulfide bonds. Host-vector systems include but are not limited to the following: bacteria transformed with bacteriophage DNA, plasmid DNA, or cosmid DNA; microorganisms such as yeast containing yeast vectors; vertebrate cell systems infected with virus (e.g., vaccinia virus, adenovirus, and the like); insect cell systems infected with virus (e.g., baculovirus) or avian embryonic cells inoculated with the recombinant nucleic acid. The expression elements of these vectors vary in their strength and specificities. Depending upon the host-vector system utilized, any one of a number of suitable transcription and translation elements can be used.

Once the novel isolated iFABP gene expression control region of the present invention has been cloned into a vector system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like. Alternatively, it is contemplated that the incorporation of the DNA of the present invention into a recipient cell may be by any suitable method such as, but not limited to, viral transfer, electroporation, gene gun insertion, sperm mediated transfer to an ovum, via microinjection techniques, and the like.

Another aspect of the present invention, therefore, is a method of expressing a heterologous polypeptide in a eukaryotic cell by transfecting the cell with a recombinant DNA comprising the avian iFABP gene expression control region operably linked to a nucleic acid insert encoding a polypeptide and, optionally, a polyadenylation signal sequence, and culturing the transfected cell in a medium suitable for expression of the heterologous polypeptide under the control of the avian iFABP gene expression control region.

In one embodiment of the method of the present invention, the recipient eukaryotic cell is derived from an avian. In one embodiment, the avian is a chicken.

Yet another aspect of the present invention is a eukaryotic cell transformed with an expression vector according to the present invention and described above. In one embodiment of the present invention, the transformed cell is a chicken gut-specific cell and the nucleic acid insert comprises the avian iFABP gene expression control region, a nucleic acid insert encoding an avian codon optimized polypeptide for expression in an avian cell, and an SV40 polyadenylation sequence.

It is contemplated that the transfected cell according to the present invention may be transiently transfected, whereby the transfected recombinant DNA or expression vector may not be integrated into the genomic nucleic acid. It is further contemplated that the transfected recombinant DNA or expression vector may be stably integrated into the genomic DNA of the recipient cell, thereby replicating with the cell so that each daughter cell receives a copy of the transfected nucleic acid. It is still further contemplated for the scope of the present invention to include a transgenic animal producing a heterologous protein expressed from a transfected nucleic acid according to the present invention.

In one embodiment of the present invention, the transgenic animal is an avian selected from a turkey, duck, goose, quail, pheasant, ratite, an ornamental bird or a feral bird. In another embodiment, the avian is a chicken and the heterologous protein produced under the transcriptional control of the isolated avian iFABP gene expression control region according to the present invention is produced in the avian gut tissue.

Viral Vector Cell Transformation

An exemplary approach for the in vivo introduction of a nucleic acid encoding the subject novel isolated iFABP gene expression control region into a cell is by use of a viral vector containing nucleic acid, e.g., a cDNA, encoding the gene product. Infection of cells with a viral vector has the advantage that a large proportion of the targeted cells can receive the nucleic acid. Additionally, molecules encoded within the viral vector, for example by a cDNA contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo. These vectors provide efficient delivery of genes into cells, and the transferred nucleic acids are stably integrated into the chromosomal DNA of the host. Recombinant retrovirus can be constructed in the part of the retroviral coding sequence (gag, pol, env) that has been replaced by nucleic acid encoding avian iFABP gene expression control regions, thereby rendering the retrovirus replication defective. Protocols for producing recombinant retroviruses and for infecting cells in vitro or in vivo with such viruses can be found in Molecular Biology references, such as Sections 9.10–9.14 in *Current Protocols in Molecular Biology*, Ausubel et al., eds. (1989, Greene Publishing Associates) and other standard laboratory manuals. Examples of suitable retroviruses include pLJ, pZIP, pWE and pEM which are all well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example, PCT publications WO93/25234, WO94/06920, and WO94/11524). For instance, strategies for the modification of the infection spectrum of retroviral vectors include coupling antibodies specific for cell surface antigens to the viral env protein (Roux et al., 1989, *Proc. Natl. Acad. Sci.* 86: 9079–9083; Julan et al., 1992, *J. Gen. Virol.* 73: 3251–3255; and Goud et al., 1983, *Virology* 163: 251–254) or coupling cell surface ligands to the viral env proteins (Neda et al., 1991, *J. Biol. Chem.* 266: 14143–14146; which are all incorporated herein by reference in their entireties). Coupling can be in the form of the chemical cross-linking with a protein or other moiety (for example, lactose used to convert the env protein to an asialoglycoprotein), as well as by generating fusion proteins (e.g., single-chain antibody/env fusion proteins). This technique, while useful to limit or otherwise direct the infection to certain tissue types, can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., 1988, *BioTechniques* 6: 616; Rosenfeld et al., 1991, *Science* 252: 43 1434; and Rosenfeld et al., 1992, *Cell* 68: 143–155, all of which are incorporated herein by reference in their entireties). Suitable adenoviral vectors derived from the adenovirus strain Ad type 5 dl324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, for example, Jones et al., 1979, *Cell* 16:683; Berkner et al., supra; and Graham et al., pp. 109–127 in *Methods in Molecular Biology*, vol. 7, 1991, Humana Publishers, Clifton, N.J.; all of which are incorporated herein by reference in their entireties). Expression of an inserted gene such as, for example, encoding the human interferon α2b, can be under control of the exogenously added iFABP gene expression control region sequence.

Yet another viral vector system useful for delivery of, for example, the subject avian iFABP gene expression control region operably linked to a nucleic acid encoding a polypeptide is the adeno-associated virus (AAV). Vectors containing as little as 300 base pairs of AAV can be packaged and can integrate. Space for exogenous DNA is limited to about 4.5 kb. An AAV vector, such as that described by Tratschin et al., in *Mol. Cell. Biol.* 5:3251–3260 (1985) can be used to introduce DNA into cells. A variety of nucleic acids have been introduced into different cell types using AAV vectors (see, for example, Hermonat et al., 1984, *Proc. Natl. Acad. Sci.* 81:6466–6470; Tratschin et al., 1985, *Mol. Cell. Biol.* 4:2072–2081; Wondisford et al., 1988, *Mol. Endocrinol.* 2:32–39; Tratschin et al., 1984, *J. Virol.* 51:611–619; and Flotte et al., 1993,*J. Biol. Chem.* 268:3781–3790; all of which are incorporated herein by reference in their entireties).

Other viral vector systems useful in the present invention included ALV (see, for example, WO 99/19472 to Ivarie et al); MuLV (Mizuarai et al, 2001, *Biochem. Biophys. Res. Comm.* 286: 456–463); REV (WO 97/47739 to MacArthur); and the like.

Non-Viral Expression Vectors

Most non-viral methods of gene transfer rely on normal mechanisms used by eukaryotic cells for the uptake and intracellular transport of macromolecules. In preferred embodiments, non-viral gene delivery systems of the present invention rely on endocytic pathways for the uptake of the subject iFABP gene expression control region and operably linked polypeptide-encoding nucleic acid by the targeted cell. Exemplary gene delivery systems of this type include liposomal derived systems, poly-lysine conjugates, and artificial viral envelopes.

In a representative embodiment, a nucleic acid comprising the novel isolated iFABP gene expression control region of the present invention can be entrapped in liposomes bearing positive charges on their surface (e.g., lipofectins) and which may optionally be tagged with antibodies against cell surface antigens of the target tissue (for example, Mizuno et al., 1992, NO Shinkei Geka 20:547–551 and WO 91/06309, incorporated herein by reference in their entireties).

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180, all of which are incorporated herein by reference in their entireties). It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al., 1993, Science 260–926; Wagner et al., 1992, *Proc. Natl. Acad. Sci.* 89:7934; and Christiano et al., 1993, *Proc. Natl. Acad. Sci.* 90:2122, all of which are incorporated herein by reference in their entireties). It is further contemplated that a recombinant DNA molecule comprising the novel isolated iFABP gene expression control region of the present invention may be delivered to a recipient host cell by other non-viral methods including by gene gun, microinjection, sperm-mediated transfer, or the like.

Transgenic Animals

Also contemplated to be within scope of the present invention are transgenic animals, such as chickens, containing a transgene comprising the novel isolated iFABP gene expression control region of the present invention and which, optionally, expresses a heterologous gene in one or more cells in the animal. Suitable methods for the generation of transgenic avians having heterologous DNA incorporated therein are described, for example, in WO 99/19472 to Ivarie et al and incorporated herein by reference in its entirety.

In various embodiments of the present invention, the expression of the transgene may be restricted to specific subsets of cells, tissues, or developmental stages utilizing, for example, cis-acting sequences acting on the iFABP gene expression control region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

One embodiment of the present invention, therefore, is a transgenic avian having a heterologous polynucleotide sequence comprising a nucleic acid insert encoding the heterologous polypeptide and operably linked to the novel isolated avian iFABP gene expression control region. In an embodiment of the present invention, the transgenic avian is selected from a chicken, a turkey, a duck, a goose, a quail, a pheasant, a ratite, an ornamental bird or a feral bird. In another embodiment of the present invention, the transgenic avian is a chicken.

In still another embodiment of the transgenic avian of the present invention, the transgenic avian includes an avian iFABP gene expression control region comprising the nucleic acid sequence in SEQ ID NO: 1, or a degenerate variant thereof.

In yet another embodiment of the transgenic avian of the present invention, the transgenic avian further comprises a polyadenylation signal sequence.

In still yet another embodiment of the transgenic avian of the present invention, the polyadenylation signal sequence is derived from the SV40 virus.

In another embodiment of the transgenic avian of the present invention, the nucleic acid insert encoding a polypeptide has a codon complement optimized for protein expression in an avian.

In another embodiment of the transgenic avian of the present invention, the transgenic avian produces the heterologous polypeptide in the gut of an avian.

In another embodiment of the transgenic avian of the present invention, the transgenic avian produces the heterologous polypeptide in the intestinal tissue of an avian.

A recombinant nucleic acid of the present invention comprising the avian gut-specific promoter of the present invention may be useful to generate a transgenic bird. A recombinant nucleic acid comprising an avian gut-specific promoter of the present invention may be transfected into a recipient the bird, thereby generating a transgenic bird having a heterologous nucleic acid in at least some of the cells thereof. In one embodiment of the present invention, the promoter is isolated from the same species of bird as the bird that is to receive the recombinant nucleic acid.

It is contemplated that a recombinant nucleic acid of the present invention may be introduced into a transfected cell in accordance with any means conventional in the art, such as calcium-phosphate precipitation, detergent-DNA complexes, DNA-DEAE ion exchange resin complexes, osmotic shock, microinjection, and viral vectors.

In one embodiment of the present invention wherein the transgenic bird is a chicken, the avian gut-specific promoter is a chicken promoter; wherein the transgenic bird is a turkey, the avian gut-specific promoter is a turkey promoter; wherein the transgenic bird is a quail, the avian gut-specific promoter is a quail promoter; wherein the transgenic bird is a duck, the avian gut-specific promoter is a duck promoter; wherein the transgenic bird is a pigeon, the avian gut-specific promoter is a pigeon promoter; wherein the transgenic bird is a goose, the avian gut-specific promoter is a goose promoter; wherein the transgenic bird is a guinea fowl, the avian gut-specific promoter is a guinea fowl promoter; and wherein the transgenic bird is a pheasant, the avian gut-specific promoter is a pheasant promoter.

It is further contemplated by the present invention that, when the recipient avian is of one species, the heterologous promoter is derived from a different avian species wherein the promoter is operable in the heterologous recipient species. The heterologous promoter may be of limited efficiency when compared to the same promoter introduced into a homologous avian species. In another embodiment of the present invention, a transgenic chicken is contemplated wherein the transgenic chicken comprises a recombinant nucleic acid having a chicken intestinal fatty acid binding protein promoter, or combinations, or fragments thereof.

A transgenic bird may be prepared according to the present invention using any transgenic method recognized by the art, such as that of Bosselman et al., U.S. Pat. No. 5,162,215, incorporated herein by reference. One suitable method for producing a transgenic bird includes transfecting a bird with a vector comprising a recombinant nucleic acid of the present invention. In one embodiment, the vector is a viral vector such as avian leukosis virus (ALV), reticuloendotheliosis virus (REV), rous sarcoma virus (RSV), Moloney murine leukemia virus (MuLV) or replication-defective vectors derived from these viruses.

Another aspect of the present invention is a method of generating a transgenic chicken comprising the steps of forming the recombinant nucleic acid, transfecting the bird with the recombinant nucleic acid, and then developing the embryo to a hatched chick.

In one embodiment of the method of the present invention, fertile eggs are placed large end up so the yolk will reorient and the blastoderm will be approximately beneath the eggshell. The surface of the egg may be wiped with a sterile gauze soaked in an antiseptic, such as ethanol, and a small hole is drilled into the shell. The vector comprising the recombinant nucleic acid is injected into the area beneath or around the blastoderm. The surface of the egg-shell is wiped once again with an antiseptic and the hole in the shell is sealed by any suitable method known in the art. The eggs may then be placed in a standard incubator and allowed to hatch. Chicks are supplied with water and standard chick food, and are caged in standard chick housing.

In one embodiment, after a hole is drilled in the egg-shell without breaking the underlying eggshell membrane, an aqueous liquid may be deposited through the opening in the shell such that the membrane is completely covered with liquid. A vector comprising the recombinant nucleic acid of the present invention is then microinjected through the cell membrane.

In yet another embodiment, chicks may be injected intra-abdominally with a vector comprising the recombinant nucleic acid one day after hatching. Chicks are supplied with water and standard chick food, and are caged in standard chick housing. The presence of the structure sequence of the recombinant nucleic acid or its product may be detected in the bird by any means known in the art. Suitable methods of detection include blot hybridization analysis, or detection of the polypeptide expressed by the heterologous recombinant nucleic acids by methods capable of distinguishing gene products, such as radioimmunoassays and enzyme assays.

The present invention is also directed toward methods of obtaining a polypeptide comprising the steps of forming a recombinant nucleic acid comprising the avian and/or gut-specific promoter and the structural sequence for a polypeptide, transfecting a bird with the recombinant nucleic acid, allowing the recombinant nucleic acid to be expressed thereby producing a polypeptide, and isolating the polypeptide from the bird. The step of isolating the polypeptide from the bird comprises obtaining tissue containing the expressed polypeptide from the bird, disrupting the tissue, and purifying the desired polypeptide using art-recognized processes. Suitable purification processes include ion exchange chromatography, absorption chromatography, molecular sieve chromatography, affinity chromatography, electrophoresis, electrofocusing, high performance liquid chromatography, and mixtures thereof.

The present invention is further illustrated by the following examples, which are provided by way of illustration and should not be construed as limiting. The contents of all references, published patents and patents cited throughout the present application are hereby incorporated by reference in their entireties.

EXAMPLE 1

Molecular Cloning of a Chick iFABP cDNA Fragment

Total RNA was extracted from the small intestine of an adult female chicken (*Gallus gallus*) by using Tri Reagent™ (Molecular Research Center Inc., Cincinnati, Ohio). The first strand cDNA was obtained by reverse transcription using oligio-deoxythymidine (12–18 mer, Amersham-Pharmacia) as the primer and Superscript™ II reverse transcriptase (GIBCO-BRL). A DNA fragment of the cFABP2 gene was amplified from the chick genomic DNA by polymerase chain reaction (PCR) using a high fidelity Taq polymerase (ExTaq™; Takara Shuzo Co. Ltd., Tokyo) and the primers FABPI-Fwl, 5'-GAGAACTATGAGAAGT-TCATGG-3' (SEQ ID NO: 6); and FABPI-Rv2, 5'-ACT-TGAATTTGTTTCCNTCYTG-3' (SEQ ID NO: 7). The primers were designed by comparing the iFABP cDNA sequences of human (Genbank accession number: M18079), mouse (M65033), rat (J00732) and Xenopus (L19946). The PCR was manually hot-started and performed at 95° C. for 30 secs, 56° C. for 30 secs, 72° C. for 45 secs for 35 cycles. A part of the PCR products was analyzed by 4% polyacrylamide gel electrophoresis, in which a single band of approximately 120 bps was seen. This 120 bp PCR product was then T/A-subcloned into the cloning vector, pGEM-T Easy (Promega) and the sequence was determined.

EXAMPLE 2

Cloning of an Intron of Chick iFABP Gene

Chicken genomic DNA was obtained from the hepatic tissue of an adult female chicken by an ordinary method. Briefly, tissue pieces were digested with RNaseA and proteinase K, and genomic DNA was purified by phenol/chloroform extraction followed by ethanol precipitation. The PCR primers, specific to the chick iFABP gene and designed according to the sequence of the cDNA, were FABPI-Fw2: 5'-TGAGTACTATGAGAAGTTCATG-GAAGCAATG-3' (SEQ ID NO: 8) and FABPI-Rv2: 5'-TC-CTGCAGAATAGTAAGCTTCAGATTATCGTG-3' (SEQ ID NO: 9). The chicken iFABP gene fragment that contained the first intron was amplified from the chicken genomic DNA by PCR using Takara LA-Taq and by following a standard protocol for the enzyme. As a result, a single-band product of approximately 600 bp size was obtained and T/A-cloned into pGEM-T Easy. The nucleic acid sequence was then determined.

EXAMPLE 3

Cloning of the 5'-Flanking Region of Chicken iFABP Gene

The 5'-flanking region of chicken iFABP gene was amplified by suppression PCR, as described in Diatchenko et al., Methods Enzymol., 303:349–380 (1999), followed by nested PCR. Briefly, chicken genomic DNA was digested by Hind III because Southern blot analysis of genomic DNA using a 5' fragment of the first intron of the chick iFABP gene indicated that Hind III digestion gave a single hybridizing band of about 2 kb. The Hind III-digested genomic DNA was treated with Klenow fragment to blunt-end the cleaved genomic fragments, and an adapter DNA (the Adapter 1 of the Smart™ PCR Substraction Kit, Clontech) was ligated to it. After filling the 3' end of the adapter by ExTaq DNA polymerase at 75° C. for 5 min, the 5'-flanking region of the chick iFABP gene was amplified by suppression PCR using ExTaq polymerase, PCR1 primer: 5'-TAATACGACTCACTATAGGGC-3' (SEQ ID NO: 10) and the cFABPI-Rv3b primer: 5'-GTGCAAGGGCAAAAT-AGCAGAC-3' (SEQ ID NO: 11) biotin-labeled at the 5' at 95° C. for 30 secs, 65° C. for 1 min, 68° C. for 5 mins for 30 cycles.

The PCR products, having the two primer sequences at opposite ends of the PCR product, were purified using streptavidin-conjugated magnet particles (Magnesphere, Promega), and amplified again by nested PCR using the primers PCR1N1: 5'-CTAATACGACTCACTAT-AGGGCTCG-3' (SEQ ID NO: 12) and cFABPI-Rv4: 5'-TTCCGCCGTAGTGGTATCCTGC-3' (SEQ ID NO: 13) using the same conditions as with the first PCR amplification. The PCR products were analyzed on a 1% agarose gel, in which a single band of about 1.6 kbp was observed. The product was T/A-cloned into pGEM-T Easy, and its sequence determined.

EXAMPLE 4

Partial Coding Sequence of Chick iFABP cDNA and Encoded Polypeptide

The N-terminal 42 amino acid sequence (SEQ ID NO: 14) of the chick iFABP gene product was determined from the cDNA and corresponding genomic DNA sequence (SEQ ID NO: 1). The sequence showed high similarity (70–86%) when compared to mammalian, frog, and zebra fish iFABP nucleic acid sequences, confirming that this clone was the chick homologue of the iFABP gene. It shows less similarity (<20%) to the other members of FABP family, as shown in FIG. 1. The position of the first intron is conserved in frog, chick, and mammals, although the lengths differ. The size in chick (0.63 kb) is intermediate to that of the frog (0.25 kbp) and the mammals (mouse and human, 1.2 kb).

EXAMPLE 5

Plasmid DNAs for the Transformation of Cells

Fragments of DNA containing predicted cis-promoter regions were amplified from plasmid DNA by PCR using Pfu DNA polymerase (Stratagene), cFABPI-Rv6: 5'-CTTTCTGTCTGTAGGCAGACTTC-3' (SEQ ID NO: 15) as the reverse primer and any of three forward primers: PCR1N1 (SEQ ID NO: 12), cFABPI-Fw5: 5'-TTTCAAAATGAACCTGAGTGG-3' (SEQ ID NO: 16) and cFABPI-Fw6: 5'-CAGTGGATCCTTCATCTCATGC-3' (SEQ ID NO: 17). The PRC products with approximately 1.5 kb, 1 kb and 0.5 kb long, respectively, and were subcloned into the pGL3-basic vector (Promega) at the Sma I site.

Cis-promoter regions for the mouse intestinal fatty acid binding protein gene were also amplified by PCR using mFABPI-Fw: 5'-TGTCTATAGAGGTAGAAAGCAGC-3' (SEQ ID NO: 18) and mFABPI-Rv: 5'-GTGTCTCTAG-GAAAGCAGAGGTC-3' (SEQ ID: NO: 19) from genomic DNA obtained from the liver of an c57B1 mouse and was inserted into pGL3 vector. The plasmid DNAs were amplified in E. coli strain XL1-Blue (Strategene) and purified with the Jetstar Maxiprep DNA purification kit (Genomed GmbH, Bad Oeynhausen). The pGL-3 promoter and pRL-SV40 (Promega) were also prepared and serve as a positive control and as a standard for the efficiency of transformation, respectively.

EXAMPLE 6

Cell Culture, Transfection, and Reporter Assay

IEC6 cells derived from rat duodenum, CaCo2 cells from mouse colon, and MCF10A cells from human breast epithelium were grown in T-75 flasks in a 5% $CO_2$ atmosphere at 37° C., as described by Quaroni et al., 1978, *Proc. Natl.*

*Acad. Sci. USA*, 75: 5548–5552; Field et al., 1987, *J. Lipid Res.,* 28:1057–1066; and Wang et al., 1997, *Anticancer Res.,* 17: 4387–4394, incorporated herein by reference in their entireties. CaCo2 cells were cultured in Dulbecco's modified Eagle's medium (DMEM) with 4.5 g/l glucose and sodium pyruvate supplemented with 10% fetal bovine serum (Harlan Bioproduct), 2 mM glutamine, 1% non-essential amino acids, and antibiotics (100 U/ml penicillin and 100 mg/ml streptomycin). IEC6 cells were cultured in DMEM with 5% fetal bovine serum, 4 mM glutamine, 10 mg/ml insulin, and antibiotics (100 U/ml penicillin and 100 mg/ml streptomycin). MCF10A cells were cultured in medium comprising Ham's F12 and DMEM (vol 1:1). The media was supplemented with 5% horse serum (Nova-Tech), 2 mM glutamine, antibiotic/antimycotic (Gibco-BRL), 0.5 µg/ml hydrocortisone, 20 ng/ml EGF, and 10 µg/ml insulin.

Prior to the transfection study, cells were inoculated into 24 well plates at appropriate densities and cultured for 24 hrs to obtain 50% confluent cultures (CaCo2 cells were at $8\times10^4$ cells/well, IEC6 cell were at $6\times10^4$ cells/well, and MCF10A cells were at $2\times10^4$ cells/well). Subsequently cells were transferred to fresh media, with the CaCo2 cells being placed in media containing 20% FBS. Transfection and reporter assays were performed using Fugene 6 (Roche) and Dual Luciferase Reporter Assay (Promega) kits. After incubation of the cells for about 1 to about 2 hrs, the mixture of Fugene 6 (Roche) and DNA (0.25 µg/well) was applied to the cells. The cells were incubated with DNA for 48 his and harvested according to the manufacturer's protocol. The reporter activity data was calculated as the ratio of firefly luciferase:R. luciferase.

EXAMPLE 7

Promoter Activity of 5'-Flanking Region of Chick iFABP Gene in Cell Lines

The gene promoter activity of the 5'-flanking region of the chick and mouse iFABP genes was assessed in the gut epithelial cell lines CaCo2 derived from mouse colon and IEC-6 derived from rat duodenum, and an extra-intestinal cell line, MCF-10A derived from human mammary epithelium. Both the mouse iFABP promoter and the 5'-flanking region of chick iFABP gene demonstrated high promoter activity in the two small intestinal epithelial cells, but not in MCF-10A, as shown in FIG. 4. While not being bound by any one theory, the results indicate that the 5'-flanking regions contain iFABP promoters that direct gut-specific expression, and that the promoter mechanism is conserved in chick and mammals. In addition, the proximal 0.5 kbp showed high promoter activity, while longer (1.1 and 1.6 kb) 5'-flanking sequences showed modest promoter activity. No difference was observed in the nucleic acid sequences of the proximal 0.5 kbp of iFABP promoter and luciferase coding region of the vector in the three iFABP promoter-pGL3 constructs. While not being bound by any one theory, the data indicates the involvement of distal, i.e. greater than 0.5 kb upstream of the transcription starting site, region in the regulation of iFABP gene expression. In particular, the distal 0.6 kb region (0.5–1.1 kb) apparently contains a suppressive element that negatively regulates iFABP expression in the cell lines used.

The mouse iFABP gene promoter in situ and the 1.2 kb of rat iFABP cis-promoter in mice and frog direct high expression of the gene in duodenum, jejunum, and ileum, and minimal, if not completely negative, expression in the caecum and colon. The distal 0.6 kbp (0.5–1.1 kb) of the chicken iFABP promoter may contribute to minimal expression of iFABP in CaCo2 cells and the colon epithelium.

IEC6 cells used in this study were not in a differentiated state, as it required more than 2 weeks for the cells to be fully differentiated after reaching confluence. iFABP gene expression was not observed in proliferating and non-proliferating undifferentiated cells in the crypts of Lieberkuhn but was seen in differentiated distal epithelium in the small intestine. While not being bound by any one theory, low iFABP promoter activity in the IEC6 cell may be correlated with the stage of the differentiation of the cells.

EXAMPLE 8

Proximal Promoter of Chick iFABP Gene

The proximal 0.3 kb of 5'-flanking region of rat iFABP promoter may be important for proper cell-type-specific expression of the gene. By comparing this region of the chick, frog, and mammals (human, rat, and mouse), 4 elements in which more than 4 consecutive nucleotides are conserved among these animals were found in the chick iFABP (SEQ ID NOS: 1 and 2) (the elements are shown with dots above the sequence SEQ ID NO: 1 in FIG. 2). In the chicken, one is the TAAAT sequence, which is believed to form a TATA-like box, located 56 bp upstream of the putative ATG translation initiation codon. The GATA sequence is just upstream of the TATA-like box and forms a consensus binding site for GATA factors. The A/T)GATA (A/G) or related sequence appear to allow the binding of GATA-4, -5, and -6 followed by the activation of iFABP gene expression in the small intestine.

The sequence CCACATCA is located 40 bp upstream of TATA-box. The fourth conserved element is the CATCA sequence located 167 bp upstream of TATA-box. This sequence is believed to be a part of the element responsible for suppression of iFABP gene expression in the ileum and the crypt. The fourth conserved sequence is very similar to the third conserved sequence.

Additional embodiments and modifications within the scope of the claimed invention will be apparent to one of ordinary skill in the art. Accordingly, the scope of the present invention shall be considered in the terms of the following claims, and is understood not to be limited to the details of the methods described in the specification.

REFERENCES CITED

Alpers, D. H., Strauss, A. W., Ockner, R. K., Bass, N. M., Gordon, J. I., 1984. Cloning of a cDNA encoding rat intestinal fatty acid binding protein. Proc. Natl. Acad. Sci. USA 81, 313–317.

Ametani, A., Hachimura, S., Yamamoto, Y, Shimizu, M., Imaoka, A., Yi, H. K., Hashimoto, K., 1996. Consecutive events of growth, differentiation and death of the small intestinal epithelial cell line, IEC-6. In Vitro Cell Dev. Biol. Anim. 32(3): 127–130

Andre, M., Ando, S., Ballagny, C., Durliat, M., Poupard, G., Briancon, C. Babin, P. J., 2000. Intestinal fatty acid binding protein gene expression reveals the cephalocaudal patterning during zebrafish gut morphogenesis. Int. J. Dev. Biol. 44:249–252.

Beck, C. W. and Slack, J. M., 1999. Gut specific expression using mammalian promoters in transgenic *Xenopus laevis*. Mech. Dev. 88(2):221–227.

Besnard, P., Niot, I., Bernard, A., Carlier, H., 1996. Cellular and molecular aspects of fat metabolism in the small intestine. Proc. Nutr. Soc. 55(1B):19–37.

Diatchenko, L., Lau, Y. F., Campbell, A. P., Chenchik, A., Moqadam, F., Huang, B., Lukyanov, S., Lukyanov, K., Gurskaya, N., Sverdlov, E. D., Siebert, P. D., 1996. Suppression subtractive hybridization: a method for generating differentially regulated or tissue-specific cDNA probes and libraries. Proc. Natl. Acad. Sci. USA 93(12): 6025–6030.

Diatchenko, L., Lukyanov, S., Lau, Y. F., Siebert, P. D., 1999. Suppression subtractive hybridization: a versatile method for identifying differentially expressed genes. Methods Enzymol. 303:349–380.

Field, F. J., Albright, E., Mathur, S. N., 1987. Regulation of cholesterol esterification by micellar cholesterol in CaCo-2 cells. J. Lipid Res. 28(9):1057–1066.

Gao, X., Sedgwick, T., Shi, Y. B., Evans, T., 1998. Distinct functions are implicated for the GATA-4, -5, and -6 transcription factors in the regulation of intestine epithelial cell differentiation. Mol. Cell Biol. 18(5):2901–2911.

Gordon, J. I., Alpers, D. H., Ockner, R. K., Strauss, A. W., 1983. The nucleotide sequence of rat liver fatty acid binding protein mRNA. J. Biol. Chem. 258:3356–3363.

Green, R. P., Cohn, S. M., Sacchettini, J. C., Jackson, K. E., Gordon, J. I., 1992. The mouse intestinal fatty acid binding protein gene: nucleotide sequence, pattern of developmental and regional expression, and proposed structure of its protein product. DNA Cell Biol. 11(1): 31–41.

Hayasaka, K., Himoro, M., Takagi, G., Takahashi, E. I., Minishima, S., Shimizu, N., 1993. Structure and localization of the gene encoding human peripheral myeline protein 2. Genomics 18:244–248.

Hegele, RA., 1998. A review of intestinal fatty acid binding protein gene variation and the plasma lipoprotein response to dietary components. Clin. Biochem. 31(8): 609–612.

Issemann, I. and Green, S., 1990. Activation of a member of the steroid hormone receptor superfamily by peroxisome proliferators. Nature 347:645–650.

Quaroni, A., Isselbacher, K. J., Ruoslahti, E., 1978. Fibronectin synthesis by epithelial crypt cells of rat small intestine. Proc. Natl. Acad. Sci. USA 75(11):5548–5552.

Petropoulos et al., "Appropriate in vivo expression of a muscle-specific promoter by using avian retroviral vectors for gene transfer" [corrected] [published erratum appears in *J Virol* 66: 5175, 1992] *J Virol* 66: 3391–7, 1992.

Rottman, J. N. and Gordon, J. I., 1993. Comparison of the patterns of expression of rat intestinal fatty acid binding protein/human growth hormone fugion genes in cultured intestinal epithelial cell lines and in the gut epithelium of transgenic mice. J. Biol. Chem. 268:11994–12002.

Sacchettini, J. C., Banaszak, L. J., Gordon, J. I., 1990. Expression of rat intestinal fatty acid binding protein in *E. coli* and its subsequent structural analysis: a model system for studying the molecular details of fatty acid-protein interaction. Mol. Cell. Biochem. 98(1–2):81–93.

Schmidt, G. H., Wilkinson, M. M., Ponder, B. A. J., 1985. Cell migration pathway in the intestinal epithelium: an in situ marker system using mouse aggregation chimeras. Cell 40:425–429.

Schroeder, F., Jolly, C. A., Cho, T. H., Frolov, A., 1998. Fatty acid binding protein isoforms: structure and function. Chem. Phys. Lipids 92(1):1–25.

Shi, Y. B. and Hayes, W. P., 1994. Thyroid hormone-dependent regulation of the intestinal fatty acid-binding protein gene during amphibian metamorphosis. Dev. Biol. 161 (1):48–58.

Shimizu, F., Watanabe, T. K., Shinomiya, H., Nakamura, Y, Fujiwara, T., 1997. Isolation and expression of a cDNA for human brain fatty acid-binding protein (B-FABP). Biochim Biophys Acta. 1354(1):24–28.

Simon, T. C., Roberts, L. J., Gordon, J. I., 1995. A 20-nucleotide element in the intestinal fatty acid binding protein gene modulates its cell lineage-specific, differentiation-dependent, and cephalocaudal patterns of expression in transgenic mice. Proc. Natl. Acad. Sci. USA 92(19): 8685–8589.

Sweetser, D. A., Birkenmeier, E. H., Klisak, I. J., Zollman, S., Sparkes, R. S., Mohandas, T., Lusis, A. J., Gordon, J. I., 1987. The human and rodent intestinal fatty acid binding protein genes. A comparative analysis of their structure, expression, and linkage relationships. J. Biol. Chem. 262 (33):16060–16071.

Sweetser, D. A., Hauft, S. M., Hoppe, P. C., Birkenmeier, E. H., Gordon, J. I., 1988a. Transgenic mice containing intestinal fatty acid-binding protein-human growth hormone fusion genes exhibit correct regional and cell-specific expression of the reporter gene in their small intestine. Proc. Natl. Acad. Sci. USA 85 (24):9611–9615.

Sweetser, D. A., Birkenmeier, E. H., Hoppe, P. C., McKeel, D. W., Gordon, J. I., 1988b. Mechanisms underlying generation of gradients in gene expression within the intestine: an analysis using transgenic mice containing fatty acid binding protein-human growth hormone fusion genes. Genes Dev. 2(10):1318–1332.

Wang, B., Soule, H. D., Miller, F. R., 1997. Transforming and oncogenic potential of activated c-Ha-ras in three immortalized human breast epithelial cell lines. Anticancer Res. 17(6D):4387–4394.Hegele, RA., 1998. A review of intestinal fatty acid binding protein gene variation and the plasma lipoprotein response to dietary components. Clin. Biochem. 31(8):609–612.

What is claimed is:

1. An isolated nucleic acid comprising a gene expression controlling region comprising a nucleotide sequence having at least 95% identity to nucleotides 1115 to 1626 of SEQ ID NO: 1.

2. The isolated nucleic avid of claim 1 wherein the gene expression controlling region comprises a nucleotide sequence having at least 99% identity to nucleotides 1115 to 1626 of SEQ ID NO: 1.

3. The isolated nucleic acid of claim 1 wherein the gene expression controlling region comprises the sequence of nucleotides 1115 to 1626 of SEQ ID NO: 1.

4. The isolated nucleic acid of claim 1 further comprising a nucleotide sequence encoding a polypeptide.

5. The isolated nucleic acid of claim 4 wherein the nucleotide sequence encoding a polypeptide is codon optimized for protein expression in an avian.

6. The isolated nucleic acid of claim 1 further comprising a polyadenylation signal sequence.

7. The isolated nucleic acid of claim 6 wherein the polyadenylation signal sequence is en SV40 virus polyadenylation signal sequence.

8. The isolated nucleic acid of claim 1 further comprising a vector.

9. The isolated nucleic acid of claim 8 wherein the vector is a virus.

10. An expression vector comprising a gene expression controlling region comprising a nucleotide sequence having at least 95% identity to nucleotides 1115 to 1626 of SEQ ID NO: 1.

11. The expression vector of claim 10 wherein the gene expression controlling region comprises a nucleotide sequence having at least 99% identity to nucleotides 1115 to 1626 of SEQ ID NO: 1.

12. The expression vector of claim 10 wherein the gene expression controlling region comprises nucleotides 1115 to 1626 of the sequence of SEQ ID NO: 1.

13. The expression vector of claim 10 wherein the expression vector further comprises a nucleotide sequence encoding a polypeptide.

14. The expression vector of claim 13 wherein the nucleotide sequence encoding a polypeptide is codon optimized for protein expression in an avian.

15. The expression vector of claim 10 further comprising an origin of replication.

16. An isolated host eukaryotic cell containing an expression vector which includes a gene expression controlling region comprising a nucleotide sequence having at least 95% identity to nucleotides 1115 to 1626 of SEQ ID NO: 1.

17. The host cell of claim 16 wherein the gene expression controlling region comprises a nucleotide sequence having at least 99% identity to nucleotides 1115 to 1626 of SEQ ID NO: 1.

18. The host cell of claim 16 wherein the gene expression controlling region comprises nucleotides 1115 to 1626 of the sequence of SEQ ID NO: 1.

19. The host cell of claim 16 wherein the cell is an avian cell.

20. The host cell of claim 16 wherein the cell is a chicken cell.

21. The host cell of claim 16 wherein the expression vector further comprises a nucleotide sequence encoding a polypeptide.

22. The host cell of claim 16 wherein the expression vector is a virus.

23. A meted of expressing a polypeptide in a host cell in culture comprising:
    introducing into a host cell a nucleic acid comprising a gene expression controlling region comprising a nucleotide sequence having at least 95% identity to the nucleotide sequence of nucleotides 1115 to 1626 of SEQ ID NO: 1 operably linked to a nucleotide sequence encoding a polypeptide; and
    maintaining the host cell under conditions suitable for expression of the polypeptide under the control of the gene expression control region.

24. The method of claim 23 wherein the gene expression controlling region comprises a nucleotide sequence having at least 99% identity to nucleotides 1115 to 1626 of SEQ ID NO: 1.

25. The method of claim 23 wherein the gene expression controlling region comprises nucleotides 1115 to 1626 of the sequence of SEQ ID NO: 1.

26. The method of claim 23 wherein the nucleotide sequence encoding a polypeptide is codon optimized for protein expression in an avian.

27. The method of claim 23 wherein the nucleic acid further comprises a polyadenylation signal sequence.

28. The method of claim 27 wherein the polyadenylation signal sequence is an SV40 virus polyadenylation signal sequence.

29. The method of claim 23 wherein the nucleic acid molecule further comprises a vector.

30. The method of claim 29 wherein the vector is a virus.

31. The method of claim 23 wherein the nucleic acid further comprises an origin of replication.

* * * * *

SEQUENCE LISTING

```
<160> NUMBER OF SEQ ID NOS: 19

<210> SEQ ID NO 1
<211> LENGTH: 2381
<212> TYPE: DNA
<213> ORGANISM: Gallus gallus
<220> FEATURE:
<221> NAME/KEY: 5'UTR
<222> LOCATION: (1)..(1626)
<221> NAME/KEY: exon
<222> LOCATION: (1627)..(1693)
<221> NAME/KEY: Intron
<222> LOCATION: (1694)..(2322)
<221> NAME/KEY: exon
<222> LOCATION: (2333)..(2381)

<400> SEQUENCE: 1
```

-continued

```
agcttcctgc gcagaaaagg ctgtggggtt cttgttccct cacacagctt aagcaaaatc      60
cccaagttca aaacgtcggc tgtaagagga gatggctcac ttcaaatgaa gtgaattatg     120
aaataatcat aaaacgagct ctgttggcag atcagagata acctctgctg ggacaaaatt     180
cttaaagtgt ataggtagaa caggaggtgt ttgcaactaa atggactaga ttgtaccaca     240
tttgatcttc taggagacaa aagggtctgg aaaacaaatt aattctggtg cacagtcagt     300
agcagcctgt tttgggtgca actacagcaa ctttgtttgc aacaataaca atctaagttg     360
ttttcttttc ctctttcctt aacttctgta cagtctaaag gtgaagagta gctattgagt     420
tacttccctc tgcatcctct tagccagatt agcattgatt tcaaaatgaa cctgagtgga     480
atggaaagcc acactatttt ggtatcacca gcaaagttct aaatttatag ttatacttca     540
gtaaaacctt ttgctgcagg tctggaagaa aaagaagatt atgataacac cagactagta     600
aaattcatta gttagagcca accctgttat ctgtgtgata agcaacattc atttcagcat     660
tcaggattta cattttttgaa gctaatagac agcagatttg gtgccgtcca taggaacaga     720
ctaactataa tcctgagttt agtacaagca gatttagcac cagcaaattt gctcagtttc     780
aagtagcact atcttgtggg gaagaaggag ctgagccagt gtgtgctcat ttctgcatt     840 atccttcaac atttaaaacc tgggatctat ggaaatcaaa cacgttggt aaaattcact     900 tagcagcaca tcaactactg taggaatgga cagaaacaga gcattcactg aatgggctat     960
aatatagaga atacgtagaa ggtgtcctga atttagacta cctattaaag agtgaggaca    1020
cgaatggaga atatcatcgc aatttctgta gctcagcact agactcgaag gtttctgaaa    1080
ctgaaccgag tttcccaaac tacctgtgga tgttcagtgg atccttcatc tcatgcttat    1140
tatgtggagt agaatagatt ctcaccaaat tagaatggaa aaagcagaga tttgtgtttt    1200
atctgttggg taaatacgtt ttctccagtt gtataaagac cctcccacca gtataaagtc    1260
ctatgcaaca aagaaaatgt caatacattc tcttagtctc attattattt tcattagata    1320
gccggttttt tactacaact caaataagat gaacagaatg aatgggttag tgactgttta    1380
taaagaagag taataaagat actatcatca tttgaggcaa taagggaggg agagattcag    1440
caaacagtgt gcttacaagt ggaaaacaag ttaaactaaa gtgaccccc tccttgacaa    1500 gatcaatgcc acagttgagc tttagccagc cacatcatca tgtaaattgc tttcctgata    1560
agcctgttca taaattctct ttgcaaagct ctgctactta ccagaagtct gcctacagac    1620 agaaag atg gca ttt aac ggt act tgg aaa ata gag aaa aat gag aac       1668
       Met Ala Phe Asn Gly Thr Trp Lys Ile Glu Lys Asn Glu Asn
        1               5                  10 tat gaa aaa ttc atg gaa gca atg g gtaagcctta cttttttgaa              1713
Tyr Glu Lys Phe Met Glu Ala Met
15                  20 tgccttctaa aagcaggata ccactacggc ggaatacaaa cttaagctgt tcatgaacta    1773
ccatctggct aacctgtcct tgttgtctg ctattttgcc cttgcacatt gccctgcact    1833 tatttttgaaa agactctata gaggggaata caaggaagaa aaacattctg atttttatttg   1893 cattgcgata atcttatgca tttagctaat tccagtagag gcattccagc agaaatttaa    1953
atagaattat atgtaaggaa tattattttg ataagactgt ttgaaaaatt acacaagagg    2013
gaaattgctg gtctccagtt ttgcagaaca cacatgattt gagtcatttt aacatgctag    2073
tgcttacttt aagcttgtac aaactgcctg taatatggat gtaaacataa ctatcctagt    2133
tggatagtag tttgtattac aggctgaaca ctgcctcagt gaaggtgga gaagagtaag    2193
```

```
actctgagtc agaattctgg gctaagctcc ctcaactaca gaaaaagtca caataaaaat    2253
gcaaacatga tgttctattt tgttttttctc tgcttgatgt taattgatta ttattatttt    2313 ttttttttagg cgtgaatgt gat gaa aag aaa gtt agg agc cca cga taa tct    2365
               Asp Glu Lys Lys Val Arg Ser Pro Arg     Ser
                        25                  30 gaa gct cac tat tca g                                                 2381
Glu Ala His Tyr Ser
        35

<210> SEQ ID NO 2
<211> LENGTH: 336
<212> TYPE: DNA
<213> ORGANISM: Gallus gallus
<220> FEATURE:
<221> NAME/KEY: misc_feature
<222> LOCATION: (1)..(336)
<223> OTHER INFORMATION: chick intestinal fatty acid binding protein
      promoter region

<400> SEQUENCE: 2
attattattt tcattagata gccggttttt tactacaact caaataagat gaacagaatg     60
aatgggttag tgactgttta taagaagag taataaagat actatcatca tttgaggcaa    120
taagggaggg agagattcag caaacagtgt gcttacaagt ggaaaacaag ttaaactaaa    180 gtgaccccccc tccttgacaa gatcaatgcc acagttgagc tttagccagc cacatcatca    240
tgtaaattgc tttcctgata agcctgttca taaattctct ttgcaaagct ctgctactta    300
ccagaagtct gcctacagac agaaagatgg cattta                              336

<210> SEQ ID NO 3
<211> LENGTH: 21
<212> TYPE: DNA
<213> ORGANISM: Artificial Sequence
<220> FEATURE:
<223> OTHER INFORMATION: PCR Primer

<400> SEQUENCE: 3
tttcaaaatg aacctgagtg g                                               21

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
cagtggatcc ttcatctcat g                                               21

<210> SEQ ID NO 5
<211> LENGTH: 17
<212> TYPE: DNA
<213> ORGANISM: Artificial Sequence
<220> FEATURE:
<223> OTHER INFORMATION: tissue specific element of chiFARBP

<400> SEQUENCE: 5
aagatactat catcatt                                                    17

<210> SEQ ID NO 6
<211> LENGTH: 22
<212> TYPE: DNA
<213> ORGANISM: Artificial Sequence
<220> FEATURE:
```

```
<223> OTHER INFORMATION: primer FABPI-Fw1

<400> SEQUENCE: 6
gagaactatg agaagttcat gg                                              22

<210> SEQ ID NO 7
<211> LENGTH: 22
<212> TYPE: DNA
<213> ORGANISM: Artificial Sequence
<220> FEATURE:
<223> OTHER INFORMATION: Primer FABPI-Rv2
<221> NAME/KEY: misc_feature
<223> OTHER INFORMATION: A,C,G,T

<400> SEQUENCE: 7
acttgaattt gtttccntcy tg                                              22

<210> SEQ ID NO 8
<211> LENGTH: 31
<212> TYPE: DNA
<213> ORGANISM: Artificial Sequence
<220> FEATURE:
<223> OTHER INFORMATION: Primer FABPI-Fw2

<400> SEQUENCE: 8
tgagtactat gagaagttca tggaagcaat g                                    31

<210> SEQ ID NO 9
<211> LENGTH: 32
<212> TYPE: DNA
<213> ORGANISM: Artificial Sequence
<220> FEATURE:
<223> OTHER INFORMATION: Primer FABPI-Rv2

<400> SEQUENCE: 9
tcctgcagaa tagtaagctt cagattatcg tg                                   32

<210> SEQ ID NO 10
<211> LENGTH: 21
<212> TYPE: DNA
<213> ORGANISM: Artificial Sequence
<220> FEATURE:
<223> OTHER INFORMATION: Primer PCR1

<400> SEQUENCE: 10
taatacgact cactataggg c                                               21

<210> SEQ ID NO 11
<211> LENGTH: 22
<212> TYPE: DNA
<213> ORGANISM: Artificial Sequence
<220> FEATURE:
<223> OTHER INFORMATION: Primer cFABPI-Rv3b

<400> SEQUENCE: 11
gtgcaagggc aaaatagcag ac                                              22

<210> SEQ ID NO 12
<211> LENGTH: 25
<212> TYPE: DNA
<213> ORGANISM: Artificial Sequence
<220> FEATURE:
<223> OTHER INFORMATION: Primer PCRN1

<400> SEQUENCE: 12
ctaatacgac tcactatagg gctcg                                           25
```

<210> SEQ ID NO 13
<211> LENGTH: 22
<212> TYPE: DNA
<213> ORGANISM: Artificial Sequence
<220> FEATURE:
<223> OTHER INFORMATION: Primer cFABPI-Rv4

<400> SEQUENCE: 13
ttccgccgta gtggtatcct gc                                              22

<210> SEQ ID NO 14
<211> LENGTH: 42
<212> TYPE: PRT
<213> ORGANISM: Gallus gallus
<220> FEATURE:
<221> NAME/KEY: UNSURE
<222> LOCATION: (1)..(42)

<400> SEQUENCE: 14

Met Ala Asn Asp Gly Thr Trp Lys Ile Glu Lys Asn Glu Asn Tyr Glu
1               5                   10                  15

Lys Phe Met Glu Ala Met Gly Val Asn Val Met Lys Arg Lys Leu Gly
            20                  25                  30

Ala His Asp Asn Leu Lys Leu Thr Ile Gln
        35                  40

<210> SEQ ID NO 15
<211> LENGTH: 23
<212> TYPE: DNA
<213> ORGANISM: Artificial Sequence
<220> FEATURE:
<223> OTHER INFORMATION: Primer cFABPI-Rv6

<400> SEQUENCE: 15
ctttctgtct gtaggcagac ttc                                             23

<210> SEQ ID NO 16
<211> LENGTH: 21
<212> TYPE: DNA
<213> ORGANISM: Artificial Sequence
<220> FEATURE:
<223> OTHER INFORMATION: Primer cFABPI-Fw5

<400> SEQUENCE: 16
tttcaaaatg aacctgagtg g                                               21

<210> SEQ ID NO 17
<211> LENGTH: 22
<212> TYPE: DNA
<213> ORGANISM: Artificial Sequence
<220> FEATURE:
<223> OTHER INFORMATION: Primer cFABPI-Fw6

<400> SEQUENCE: 17
cagtggatcc ttcatctcat gc                                              22

<210> SEQ ID NO 18
<211> LENGTH: 23
<212> TYPE: DNA
<213> ORGANISM: Artificial Sequence
<220> FEATURE:
<223> OTHER INFORMATION: Primer mFABPI-Fw

<400> SEQUENCE: 18

```
tgtctataga ggtagaaagc agc                                          23

<210> SEQ ID NO 19
<211> LENGTH: 23
<212> TYPE: DNA
<213> ORGANISM: Artificial Sequence
<220> FEATURE:
<223> OTHER INFORMATION: Primer mFABPI-Rv

<400> SEQUENCE: 19
gtgtctctag gaaagcagag gtc                                          23
```